(12) United States Patent
Moghe et al.

(10) Patent No.: US 8,715,718 B2
(45) Date of Patent: May 6, 2014

(54) EXTRACELLULAR MATRIX PRODUCTION FROM NANOSCALE SUBSTRATE

(75) Inventors: Prabhas V. Moghe, Basking Ridge, NJ (US); Ram Sharma, Montville, NJ (US); Marian Pereira Guelakis, Cranford, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 884 days.

(21) Appl. No.: 12/373,671

(22) PCT Filed: Jul. 11, 2007

(86) PCT No.: PCT/US2007/015898
§ 371 (c)(1),
(2), (4) Date: Feb. 8, 2010

(87) PCT Pub. No.: WO2008/008435
PCT Pub. Date: Jan. 17, 2008

(65) Prior Publication Data
US 2010/0136091 A1      Jun. 3, 2010

Related U.S. Application Data

(60) Provisional application No. 60/830,911, filed on Jul. 14, 2006.

(51) Int. Cl.
*A61K 38/39* (2006.01)
*A61K 9/70* (2006.01)
*C07K 14/00* (2006.01)

(52) U.S. Cl.
USPC ........... 424/443; 530/350; 530/395; 530/362; 514/9.4; 514/15.2

(58) Field of Classification Search
CPC ............ A61K 38/38; A61K 47/48284; A61K 47/48884; B82Y 5/00
See application file for complete search history.

(56) References Cited

U.S. PATENT DOCUMENTS

| 5,770,565 | A  | * | 6/1998  | Cheng et al. | 514/16.7 |
| 5,958,874 | A  | * | 9/1999  | Clark et al. | 514/8.2 |
| 2004/0126900 | A1 | * | 7/2004  | Barry et al. | 436/523 |
| 2004/0265391 | A1 | * | 12/2004 | Danenberg et al. | 424/490 |
| 2005/0227354 | A1 | * | 10/2005 | Sagawa et al. | 435/372 |

OTHER PUBLICATIONS

Sharma, 2006, Biomaterials, pp. 3589-3598; available online Mar. 9, 2006.*
Shin, 2002, Journal of Biomedical Material Research vol. 61, pp. 169-179.*
Mardon, 1994, FEBS Letters, vol. 340, pp. 197-201.*
Kishida, 1992, Biomaterials, vol. 13, Issue 13, pp. 924-930.*
Zheng, 2004, Langmuir, vol. 20, pp. 7215-7222.*
Takeoka, 2000, Biomacromolecules, vol. 1, pp. 290-295.*
RGD peptide datasheet [Online] Santa Cruz Biotechnology, [retrieved on Jul. 8, 2013]. Retrieved from the internet: <URL:www.scbt.com/datasheet-201176-rgd-peptide-grgdnp.html.*
Cook, 1997, Journal of Biomedical Materials Research, vol. 35, pp. 513-523.*
Berg, 2004, Langmuir, vol. 20, pp. 1362-1368.*
Takagi et al., "Structure of Integrin alpha5 beta1 in Complex with Fibronectin," EMBO Journal (2003); vol. 22, No. 18, pp. 4607-4615.
Mould et al., "Identification of Amino Acid Residues That Form part of the Ligand-binding Pocket of Integrin alpha5 beta1," The Journal of Biological Chemistry (Oct. 2, 1998); vol. 273, No. 40, pp. 25664-25672.

* cited by examiner

*Primary Examiner* — Joanne Hama
*Assistant Examiner* — Ian Dang
(74) *Attorney, Agent, or Firm* — Fox Rothschild LLP; Gerard P. Norton; Jianming Hao

(57) ABSTRACT

Compositions, methods, and kits for repair and production of extracellular matrix are provided. In the broad aspect, the composition comprises a ligand of α5β1 integrin attached to a surface of a nanoparticle composed of a protein, with a proviso that the protein is not fibronectin.

15 Claims, 14 Drawing Sheets

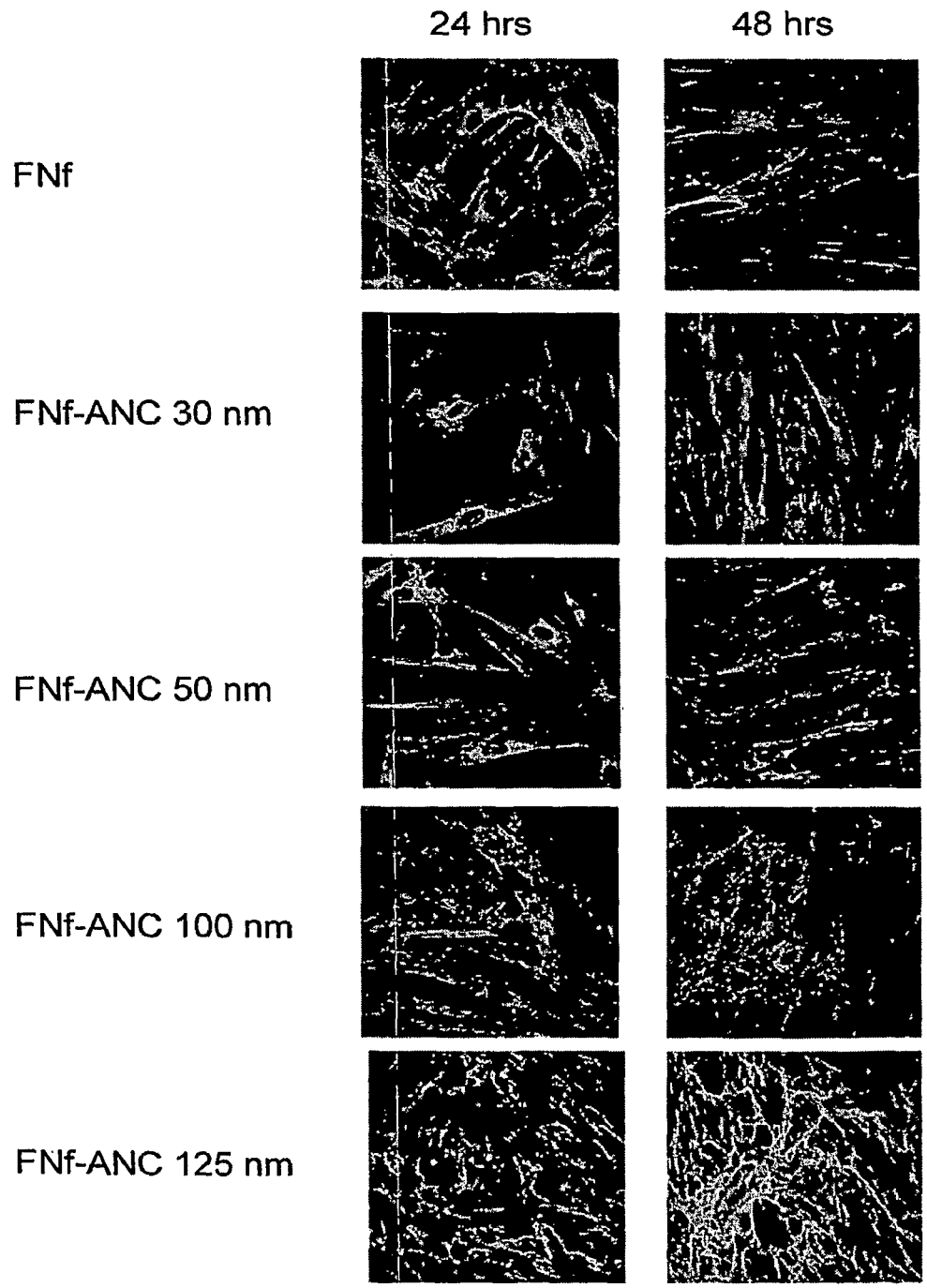

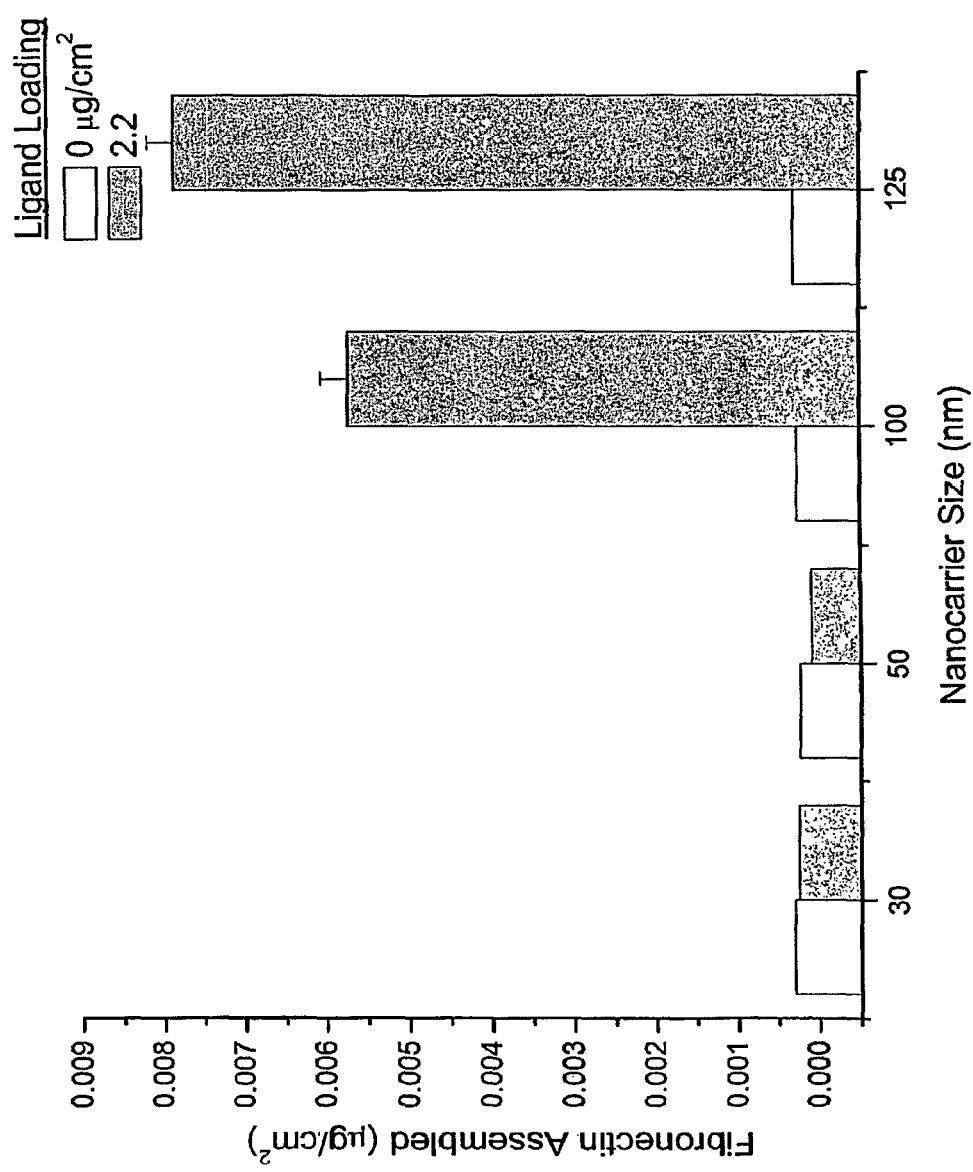

Fnf    Fnf-ANC 30 nm    Fnf-ANC 50 nm    Fnf-ANC 100 nm    Fnf-ANC 120 nm

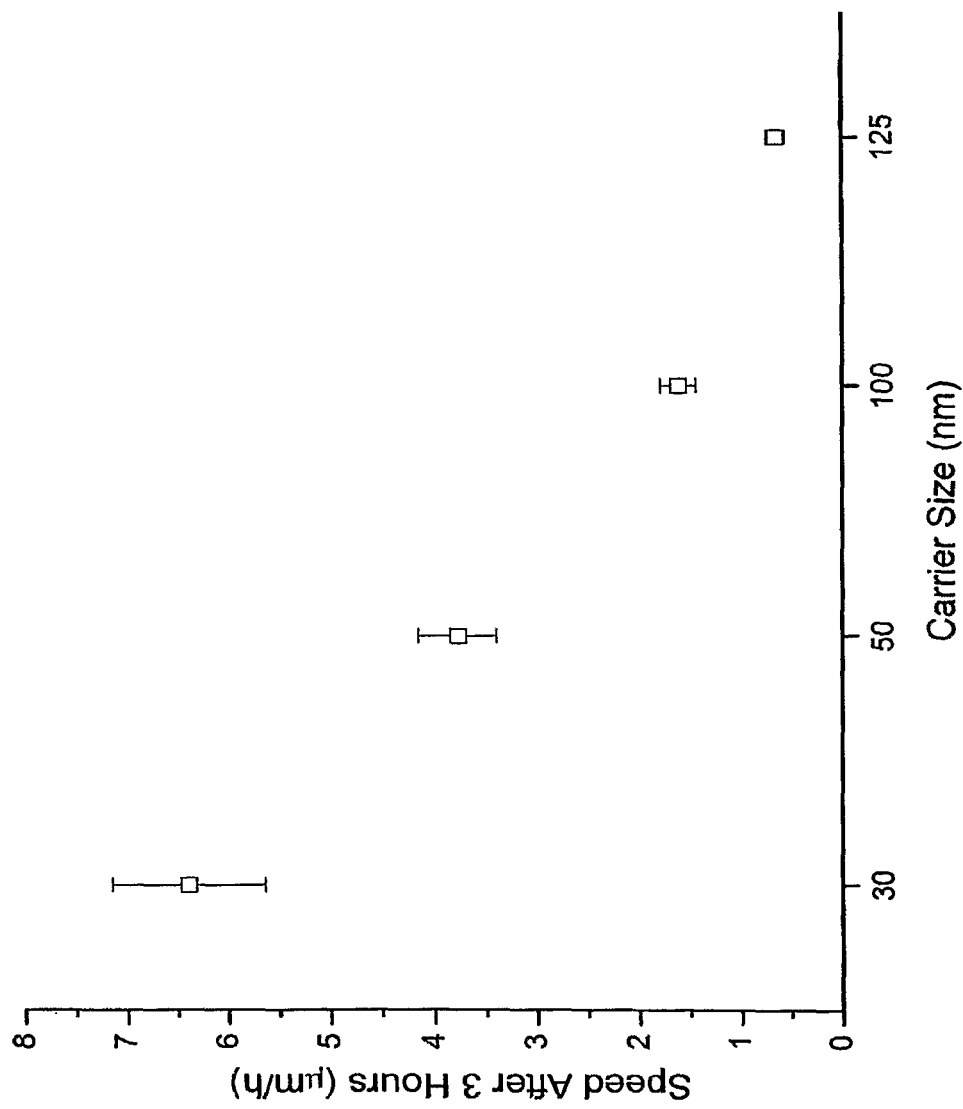

EXTRACELLULAR MATRIX PRODUCTION FROM NANOSCALE SUBSTRATE

STATEMENT OF FEDERALLY FUNDED RESEARCH

The research leading to the instant invention was supported in part by National Science Foundation Grant No. 0609000 to Prabhas V. Moghe. Accordingly, the U.S. Government may have certain rights in this invention.

CROSS-REFERENCE TO RELATED APPLICATIONS

The instant application is a National Stage filing under 35 U.S.C. §371(c) of International Application Serial No. PCT/US07/15898 filed Jul. 11, 2007, which, in turn, claims benefit of U.S. Provisional Application No. 60/830,911 filed on Jul. 14, 2006. The teaching of this application is incorporated herein by reference to the extent it is not inconsistent with the instant disclosure.

FIELD OF THE INVENTION

The instant invention relates to compositions, methods, and kits for repair and production of an extracellular matrix.

BACKGROUND OF THE INVENTION

Proper repair of tissue after injury depends on correct wound healing, a multistage process that involves different cell types for each step. Singer and Clark, *N Engl J Med*, 341(10): 738-46 (1999); Hosgood, *Vet Clin North Am Small Anim Pract*, 36(4): 667-85 (2006). Wound healing is characterized by three overlapping phases: inflammation, tissue formation, and tissue remodeling. One key event during tissue formation involves fibroblasts invading the wound space composed largely of fibrin and fibronectin, termed the provisional matrix. Clark, *Ann N Y Acad Sci*, 936: 355-67 (2001); Broughton et al, *Plast Reconstr Surg*, 117(7 Suppl): 12S-34S (2006); Corbett and Schwarzbauer, *Trends Cardiovasc Med*, 8(8): 357-62 (1998). Once the fibroblasts populate the wound site, they produce provisional secondary extracellular matrix, consisting primarily of fibronectin, tenascin, and hyaluronan, which begins the formation of granulation tissue. Ghosh et al., *Tissue Eng*, 12(3): 601-13 (2006); Mimura et al., *J Invest Dermatol*, 122(6): 1390-8 (2004).

This newly synthesized secondary matrix directs repair by supporting and regulating functions of cells recruited to the wound site including cell proliferation, migration, and angiogenesis. Eventually, collagen is deposited and the new matrix is further remodeled and contracted. Given the critical role that fibroblasts play in creating the matrix, it is important to understand what drives fibronectin secretion and assembly of fibrils.

The provisional matrix initially utilized by fibroblasts can have a positive or negative effect on the ability of fibroblasts to function. While growth factors and the matrix proteins guide the migration of fibroblasts into the provisional matrix, the assembly of the new fibronectin-rich secondary matrix that fibroblasts secrete and assemble, which begins after migration has stopped, can be driven by many cues. Riedel, K., et al., *Int J Mol Med*, 17(2): 183-93 (2006); Rumalla, and Borah, *Plast Reconstr Surg*, 108(3): 719-33 (2001); Roy, P., et al., *Cell Motif Cytoskeleton*, 43(1): 23-34 (1999). Fibrillar fibronectin assembly depends on fibronectin-integrin interactions to create a new matrix in a step-wise fashion. Mao and Schwarzbauer, *Matrix Biol*, 24(6): 389-99 (2005). First, the $\alpha 5\beta 1$ integrin binds to soluble fibronectin at the cell-binding region encompassing the synergy sequence (PHSRN) located in the $9^{th}$ type III repeat and the adjacent Arg-Gly-Asp (RGD) cell-binding sequence in the $10^{th}$ type III repeat. Aota et al, *J Biol Chem*, 269(40): 24756-61 (1994); Danen, et al., *J Biol Chem*, 270(37): 21612-8 (1995); Main, et al., *Cell*, 71(4): 671-8 (1992); Leahy et al, *Cell*, 84(1): 155-64 (1996). After the cell binds to fibronectin, molecular events leading to the reorganization of the actin cytoskeleton and activation of signaling complexes take place, leading to the elongation and stretching of fibronectin from its compact form. Finally, fibronectin-fibronectin interactions lead to assembly formation. The cytoskeleton plays a critical role during matrix assembly, as the cytoskeletal state mediates the activation of signaling events that promote the assembly of fibronectin fibrils. In the past, biochemical approaches have been used to modulate the cytoskeleton to promote assembly of fibronectin fibrils.

More recently, biophysical approaches have been used to investigate how interfaces could modulate matrix assembly. Fibroblasts have been documented to respond to both spatial and mechanical input of integrins, affecting cell shape and potentially gene expression and cell functions. Three dimensional fibronectin scaffolds have been used to examine the effect of dimensionality on matrix assembly. Chiquet, M., et al., *Matrix Biol*, 22(1): 73-80 (2003); Mao and Schwarzbauer, *J Cell Sci*, 118 (Pt 19): 4427-36 (2005); Cukierman, E., et al., *Science*, 294(5547): 1708-12 (2001).

In these studies, cell associated matrix assembly was greater in three-dimensional substrates compared to two-dimensional substrates. The degree of rigidity of the substrate, which influences the ability of the cell to contract the substrate, has been shown to play a role in matrix assembly, where rigid substrates promote better cell attachment, and allow the cells to elongate and contract, leading to greater quantities of matrix assembly compared to compliant substrates.

Given the complexity and dynamic nature of cell interactions with matrix ligands, a need exists for a better understanding of matrix-cell interactions which would lead to novel methods and compositions for tissue engineering and wound healing.

SUMMARY OF THE INVENTION

The instant invention addresses these and other needs in the art by providing, in a first aspect, a composition comprising a ligand of $\alpha 5\beta 1$ integrin attached to a surface of a nanoparticle composed of a protein, with a proviso that the protein is not fibronectin. In one embodiment, the ligand comprises a fibronectin fragment comprising domain 9 and domain 10 (also referred to as repeats "III$_9$" and "III$_{10}$" respectively, or "$9^{th}$ type III repeat" and "$10^{th}$ type III repeat", respectively). In one embodiment, the nanoparticle is comprised of albumin and has a size of between about 20 nm and about 200 nm, or preferably between about 100 nm and about 150 nm, or more preferably, between about 100 nm and about 125 nm. In different embodiments, the concentration of the ligand is at least about $2.5 \times 10^{-4}$ µg per square centimeter of the surface of the nanoparticle. In a preferred embodiment, the composition of the instant invention, when attached to a substrate, increases an assembly of fibronectin into fibronectin matrix fibrils by at least about 40%, compared to the ligand which is not attached to the nanoparticle.

In a second aspect, the invention provides a substrate comprising the composition according to any embodiment of the first aspect of the invention. The ligand may be present in a concentration of at least about 0.4 μg per square centimeter of the surface of the substrate, or preferably, at least about 1.7 μg per square centimeter of the surface of the substrate, or below about 2.2 μg per square centimeter of the surface of the substrate. In one embodiment, the concentration of the ligand bound to the nanoparticles comprises between about 1.7 μg and about 2.2 μg per square centimeter of the substrate surface.

In a third aspect, the invention provides a method of promoting an assembly of an extracellular matrix in a targeted area of a subject comprising administering to the targeted area a composition according to any embodiment of the first aspect of the invention and/or the substrate according to any embodiment of the second aspect of the invention.

In a fourth aspect, the invention provides a kit, comprising a ligand of α5β1 integrin, a nanoparticle composed of a protein, with a proviso that the protein is not fibronectin, and a set of instructions. In one embodiment, the ligand comprises a fibronectin fragment comprising domain 9 and domain 10. In different embodiments of the invention, the nanoparticle has size of between about 20 and about 200 nm, or preferably, between about 100 and 150 nm, or more preferably, between about 100 nm and about 125 nm. The kit may further optionally comprise a substrate.

BRIEF DESCRIPTION OF THE FIGURES

FIGS. 6A and B illustrate relationship between the size of the nanoparticle and extracellular matrix assembly.

FIGS. 8A-C illustrate evaluation of ANC mobility depending on the ANC's sizes (panels A and C) and seeding time (panels B and C).

DETAILED DESCRIPTION OF PREFERRED EMBODIMENTS

Figure 1:
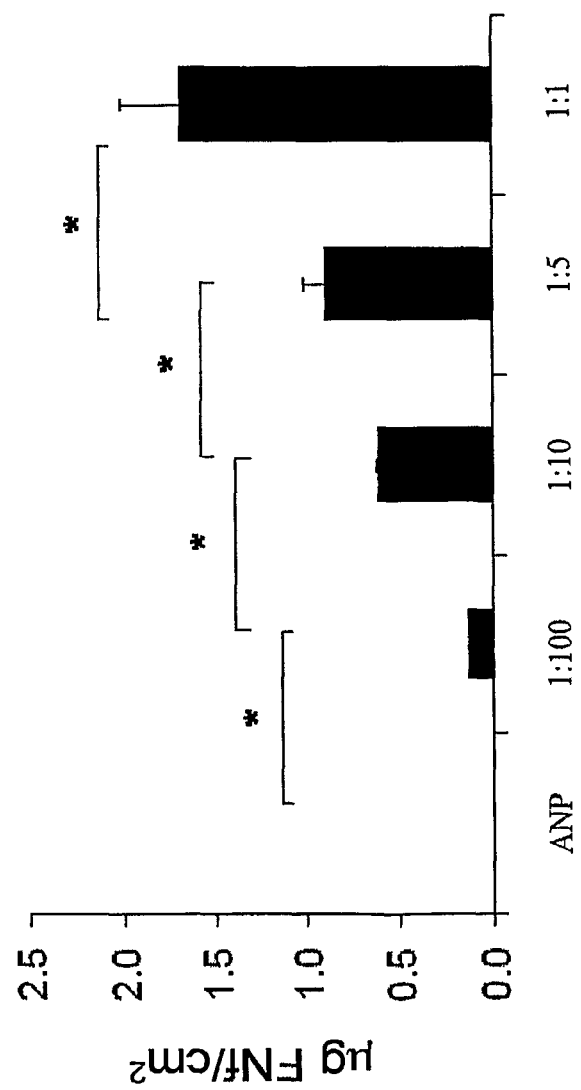
FIG. 1 illustrates an increasing display of FNf on differentially conjugated FNf-ANPs.

In a first broad aspect, the invention comprises a nanoparticle comprising a ligand of α5β1 integrin attached to a surface of a nanoparticle composed of a protein.

Nanoparticle

Suitable non-limiting examples of the proteins useful for the nanoparticle of the present invention include, without limitations, albumin, elastin and collagen. Protein nanoparticles have been known in the art. For example, albumin nanoparticles have been described in U.S. Pat. Nos. 5,133,908 and 6,117,454 and U.S. Patent Publications 20060263434, 20070010427, 20070082838, and 20070116774. The nanoparticle of the instant invention may be prepared, for example, as described in Example 1 of the instant application. Briefly, a solution of albumin having a pH of about 10.5 is heated at 80° C. for five minutes, then the pH of the solution is lowered to about 6.0 and the temperature is lowered to 37° C., and the solution is stirred. The size of the nanoparticle may be modulated by the time the stirring. Generally, the increase in the stirring time results in an increased size of nanoparticles. Thus, the nanoparticles having size from about 20 nm to about 180 nm can be produced.

Ligand

After the nanoparticle is prepared, it is conjugated with a ligand of α5β1 integrin. A suitable example of the ligand is fibronectin, which is a natural ligand of α5β1 integrin. Fibronectins are dimers of 2 similar peptides. Each chain is 60-70 nm long and 2-3 nm thick. At least 20 different fibronectin chains have been identified that arise by alternative RNA splicing of the primary transcript from a single fibronectin gene.

Fibronectins contain at least 6 tightly folded domains each with a high affinity for a different substrate such as heparan sulfate, collagen (separate domains for types I, II and III), fibrin and cell-surface receptors. The cell-surface receptor-binding domain contains a consensus amino acid sequence, RGD (SEQ ID NO: 1) located in domain 10 of fibronectin. Another important sequence is SEQ ID NO: 2 (PHSRN) which has also been known as the "synergy sequence" and which is located in domain 9 of fibronectin. Accordingly, in one embodiment, the fibronectin fragment comprises SEQ ID NO: 1 or SEQ ID NO: 2 or a combination thereof. For example, the suitable fibronectin fragment may include both domain 9 and domain 10 of the full-length fibronectin, such as, for example SEQ ID NO: 3:

GLDSPTGIDFSDITANSFTVHWIAPRATITGYRIRHHPEHFSGRPREDRV

PHSRNSITLTNLTPGTEYVVSIVALNGREESPLLIGQQSTVSDVPRDLEV

VAATPTSLLISWDAPAVTVRYYRITYGETGGNSPVQEFTVPGSKSTATIS

GLKPGVDYTITVYAVTGRGDSPASSKPISINYRT

Methods of Production of the Ligand and the Nanoparticle Protein.

Assuming that the ligand is a protein or a fragment thereof, a variety of methods exist to produce the protein used for the nanoparticle and the desired ligand. For example, the ligand may be ordered from a manufacturer, such as, for example, New England Peptide, Inc. (Gardner, Mass.). Proteins used for the nanoparticle (e.g., albumin or elastin or collagen) may be commercially obtained or purified from human blood.

In another embodiment, the amino acid sequences of the instant invention can be synthesized by standard solid peptide synthesis (Barany, G. and Merrifield, R. B., The Peptides 2:1 284, Gross, E. and Meienhofer, J., Eds., Academic Press, New York) using tert-butyloxycarbonyl amino acids and phenylac-etamidomethyl resins (Mitchell, A. R. et al., J. Org. Chem. 43:2845 2852 (1978)) or 9-fluorenylmethyloxycarbonyl amino acids on a polyamide support (Dryland, A. and Sheppard, R. C., J. Chem. So. Perkin Trans. I, 125 137 (1986)). Alternatively, synthetic peptides can be prepared by pepscan synthesis (Geysen, H. M. et al., J. Immunol. Methods 03:259 (1987); Proc. Natl. Acad. Sci. USA 81:3998 (1984)), Cambridge Research Biochemicals, Cambridge, U.K. or by standard liquid phase peptide synthesis.

In another embodiment, the amino acid sequences may be purified from a cellular or non-cellular source. The suitable sources include cells which natively express peptides containing those sequences as well as artificial expression system. The former include, without limitation, cultured fibroblasts or keratinocytes which are known to produce fibronectin. In addition, a soluble form of fibronectin is present in human blood. The purification techniques are well known in the art. One suitable method of purification is affinity chromatography. Essentially, in this technique, the cell extract is passed through a column impregnated with antibodies specifically recognizing the amino acid sequence of interest.

In yet another embodiment, the amino acid sequences and/or the nucleic acid sequences may be synthesized from recombinant sources. The mRNA and cDNA sequences of fibronectin are well known in the art and available, for example, from Genbank. Thus, the primers may be designed to multiply the nucleic acid sequence encoding the amino acid sequence of interest by PCR (if the template is cDNA) or RT-PCR (if the template is mRNA).

This nucleic acid sequence encoding the amino acid sequence of interest may be subcloned into a vector by methods well known in the art utilizing endonuclease and ligase properties. The vector may be either plasmid or viral vector. Suitable plasmid vectors include, without limitation, pUC18 and pUC 19. Suitable viral vectors include adenoviral vectors, adeno-associated vectors and baculoviral vectors. Additional examples of vectors are listed in catalogs of different manufacturers, including, without limitation, Promega Corp. (Madison, Wis.), incorporated herein by reference in its entirety.

Further, the vector may contain a promoter which directs the expression of the amino acid sequence of interest from the nucleic acid sequence. Suitable promoters include, without limitation, CMV, RSV, and TK. The vector containing the nucleic acid sequence encoding the amino acid sequence of interest is later introduced to host cells.

The choice of the host cell system depends largely on the type of the vector and the type of the promoter. In general, the host cells include, without limitations, prokaryotic, yeast, insect, and mammal cells. Essentially, the host cells should be selected based on the nature of the vector.

Suitable methods of introducing exogenous nucleic acid sequences are described in Sambrook and Russel, Molecular Cloning: A Laboratory Manual (3rd Ed., 2001), Cold Spring Harbor Press, NY. These methods include, without limitation, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors. Other methods for introducing the nucleic acid sequences of the present invention into suitable cells, such as, for example, electroporation (see, e.g., Iversen et al., Genetic Vaccines and Ther. 3: 2-14 (2005)) will be apparent to a person of ordinary skill in the art. All such methods are within the scope of the present invention.

Depending on the type of the host cell, the codons of the nucleic acid sequences encoding the amino acid sequences of the instant invention can be selected for optimal expression in prokaryotic or eukaryotic systems. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

The amino acid sequences used in the compositions and the methods of the instant invention can be purified or partially purified from cells comprising the vector, comprising the nucleic acid sequence encoding the amino acid sequence of interest (e.g., the ligand), using known purification processes such as gel filtration and ion exchange chromatography. Purification may also include affinity chromatography with agents known to bind the respective amino acid sequences.

Further, the amino acid sequences of interest may be tagged, as described in more details below. In one non-limiting example, the recombinant nucleic acid sequences are fused with a nucleic acid sequence encoding glutathione-S-transferase (GST). The GST-tag is often used to separate and purify proteins that contain the GST-fusion. GST-fusion proteins can be produced in E. coli, as recombinant proteins. The GST part binds its substrate, glutathione. Sepharose beads can be coated with glutathione, and such glutathione-sepharose beads bind GST-proteins. These beads are then washed, to remove contaminating bacterial proteins. Adding free glutathione to beads that bind purified GST-proteins will release the GST-protein in solution.

Once purified, the cleavage of the amino acid sequences of the instant invention into fragments of amino acid residues can be achieved using proteolytic enzymes such as thrombin or clostridiopeptidase B (clostripain). The exact time required for proteolysis varies with each preparation and markedly depends upon the batch of clostripain used. Therefore, the optimum time for a single cleavage must be determined for each combination of clostripain batch and the amino acid sequence used. The protein fragments resulting from either thrombin or clostripain proteolysis may be further cleaved by digestion with trypsin, which cleaves on the carboxy terminus of lysine or arginine residues.

The sequence derived from proteolytic digestion may be identified using the Edman degradation method of protein sequencing. In addition, sequence analysis of the recombinant amino acid sequence of interest may be accelerated by using an automated liquid phase amino acid sequenator, thereby allowing for the analysis of picomolar quantities of the recombinant proteins containing up to 50 amino acid residues in length.

Preparation of the Composition of the Instant Invention

The suitable fibronectin fragment (or other ligand of the α5β1 integrin) may be attached to the surface of the nanoparticle in a variety of ways, including, preferably, covalent linkage, as described in Example 2. Briefly, the ligand and the nanoparticle are independently reacted with a cross-linking reagent (e.g., succinimidyl-3-(2-pyridyldithiol)-propionate (SPDP) or analogs thereof, which may be commercially obtained, for example, from Thermo Fisher Scientific, Inc., Rockford, Ill.), one of the reactant is reduced (e.g., with DTT), and the ligand and the nanoparticle are mixed.

The —SH group of one of the reactants (e.g., the ligand) produced after treating that reactant with DTT will react with the PD moiety of the other reactant (the nanoparticle) thus resulting in the disulfide bonding between the ligand and the nanoparticle, thus resulting in the general composition of the instant invention. Modulating the ratios of the ligand and the nanoparticle, one will be able to prepare the nanoparticles according to different embodiments of the instant invention, differing by the amount of the ligand per square centimeter of the nanoparticle. For example, mixing the ligand and the nanoparticle of the instant invention in the ratio of 1:1, one would expect to produce the composition with a greater density of the ligand than mixing the ligand and the nanoparticle in the ratio of 1:100. It is estimated that in a one set of preferred embodiments, the concentration of the ligand is between about $2.5 \times 10^{-4}$ and about $1.1 \times 10^{-3}$ ng/cm$^2$ of the nanoparticle surface.

Substrates

In an embodiment of the invention, the composition according to any of the embodiments described above, is included onto a surface or within a substrate. In this disclosure, the term "surface" is used broadly, and includes both the external and internal surfaces of the substrate (e.g., if the substrate is porous). Suitable examples of substrates include, without limitation, both biodegradable and non-biodegradable materials. In one set of embodiments, the concentration of the composition of the present invention on the substrate surface is between about 0.4 μg and about 2.2 μg of the ligand per square centimeter of the surface of the substrate, e.g., between about 0.7 μg and about 1.9 μg, or between about 1.0 μg and about 1.6 μg, or about 1.3 μg.

Suitable biodegradable substrates include, without limitation synthetic polymers such as polycarbonates, polyanhydrides, polyesters; naturally derived materials such as processed collagens, basement membrane derived matrix (Matrigel™, BD Biosciences, San Jose, Calif.), and any combination thereof.

Suitable non-biodegradable substrates include, without limitation polyacrylate hydrogels, polystyrenes, polyethylenes, glass, polyurethanes, and any combination thereof.

Incorporation of the Composition into or onto the Substrate.

In one embodiment, the composition of the instant invention is suspended in a liquid (e.g., water or saline or PBS), and the resulting suspension is applied to the substrate. A person of the ordinary skill in the art will recognize that the liquid should not impair the bioactivity of the composition and that the liquid and the composition should have approximately the same density to ensure uniform distribution of the composition in the suspension. Suitable methods of application include soaking, dripping, brushing, dipping, etc. If the substrate is porous, soaking the substrate in the suspension is preferred, especially when the suspension is stirred. The time of the application may range from one hour to ten hours before the intended use (depending on the temperature of processing) and can be extended to enable storage in appropriate conditions prior to intended use. Since the synthesis and characterization of the nanoparticles requires a relatively long time (in one embodiment, up to about four days), in some embodiments, it is preferable to pre-manufacture the nanoparticles and/or adsorb these nanoparticles onto the surface of the substrate. After the manufacturing, the product can be stored before use.

Functionally immobilized nanoparticles are unable to exhibit movement or allow unhindered sequestration by cells. Examples of immobilized nanoparticles are substrate-tethered nanoparticles or grafted nanoparticles and nanoparticles covalently derivatized to substrates such as those treated with plasma-treated substrates. Non functionally immobilized nanoparticles, in contrast, are physisorbed on substrates such that strong receptor-mediated cell adhesion to the nanoparticles and cell sequestration can allow the mobility and even release of nanoparticles from the underlying substrate. Mobility of nanoparticles can be quantified by tracking individual, labeled nanoparticles via single nanoparticle tracking studies and estimating their translocation rate. Accordingly, it is important that the composition of the instant invention should not be rigidly attached to the surface of the substrate. As described in Examples of the application, immobilization of the composition of the instant invention to the surface of the substrate inhibited β1 translocation and fibronectin matrix assembly. It is preferred that the composition of the instant invention be adsorbed onto the surface of the substrate.

Methods

In a third aspect of the invention, a method for promoting formation of the extracellular matrix is provided. In a broad embodiment, the method comprises administering the composition of the instant invention to the targeted area. The composition of the instant invention may be administered in a form of a suspension or in a form of a powder. Suitable administration methods include, without limitation powdering, pouring, brushing, spraying, the composition onto the surface of the targeted area. Any other method is also suitable as long as steps are undertaken to ensure that the composition of the instant invention will be adsorbed onto a surface of the targeted area. As shown in the Examples below, providing the composition of the instant invention in a liquid medium is not as advantageous for cell adhesion, attachment and matrix formation as presenting the composition onto a substrate. Thus, in this embodiment, the surface of the targeted area serves as a substrate.

In another embodiment, a substrate is provided, such as the substrate according to the second aspect of the invention. Preferably, the substrate includes the composition of the instant invention, e.g., the composition is adsorbed on the substrate surface.

The progress may be verified by measuring multiple parameters. Among these are, without limitation, cell adhesion, cell spreading, integrin β1 organization at focal contacts, fibronectin matrix assembly, β1 integrin localization, and any combination thereof.

Kits

A person of ordinary skill in the art will appreciate that a situation may arise when it is beneficial if the components of the composition of the instant invention are provided separately, for example, if storage conditions of the ligand and the nanoparticle may be different. Accordingly, in the fourth aspect, the invention provides a kit comprising the nanoparticle composed of a protein, with a proviso that the protein is not fibronectin, and a ligand of α5β1 integrin. In another embodiment, the ligand and the nanoparticle of the kit are already conjugated to each other.

In additional embodiments, the kit may further comprise reagents necessary for conjugating the ligand onto the surface of the nanoparticle (if the nanoparticle ands the ligand are provided separately). The ligand and the nanoparticles may be pre-formulated in several containers so that a person of the ordinary skill in the art would be able to select the concentration of the ligand (e.g., micrograms of the ligand per square unit of the nanoparticle surface) which he or she intends to use. The kit may also comprise a substrate, according to the description above. The substrate may be pre-shaped to conform to the shape of the wound or it can be shaped into the desired form at the time of the administration.

The kit may also comprise a set of instruction. The medium of the set of instructions is not crucial for the instant invention, and includes, without limitation printed, electronic, video recording, audio recording and any combination thereof. The instructions preferably contain information on the safe and efficient use of the kit. For example, the instruction may comprise information on how to conjugate the ligand onto the nanoparticles, how to incorporate the ligand-bound nanoparticles onto a surface of the substrate without functionally immobilizing the nanoparticle, or any combination thereof.

Selected embodiments of the invention will now be further discussed in the following examples. The examples are illustrative only, and are not intended to limit the instant disclosure in any way.

EXAMPLES

Materials and Methods

The materials and methods described in this section are applicable to Examples 1-6 of the instant disclosure.

Cell Culture, Antibodies, and Chemical Reagents.

Human foreskin fibroblasts, HFF, a gift from Dr. Simpson-Haidaris, University of Rochester, Rochester, N.Y.) were cultured in McCoy's medium supplemented with 100 U/ml penicillin, 0.1 mg/ml streptomycin, 2 mM L-glutamine, and 10% fetal bovine serum (Invitrogen Life Technologies, Carlsbad, Calif.). In order to isolate the effect of ligand presentation in modulating fibronectin matrix assembly, HFFs were switched from serum-supplemented media to serum-free media 16-18 hours prior to the experiment. Cells were trypsinized, washed, and seeded in serum-free McCoys's medium supplemented with penicillin, streptomycin, and L-glutamine, as described above. Rho kinase inhibitor (Y27632) was obtained from Calbiochem (San Diego, Calif.), mouse anti-human integrin 151 (clone 12G10) from Chemicon International (Temecula, Calif.), and rabbit polyclonal anti-human serum albumin from Abeam (Cambridge, Mass.). Bovine serum albumin, 15-nitrophenyl N-acetyl 15-D glucosaminide, FAST OPD tablets, rabbit anti-glutathione-5-transferase (GST), horseradish peroxidase-conjugated goat anti-rabbit antibody, and monoclonal anti-human serum albumin, monoclonal anti-human fibronectin (clone IST-4) were purchased from Sigma (St. Louis, Mo.). Horseradish peroxidase-conjugated rabbit anti-albumin was obtained from MP Biomedicals (Irvine, Calif.) and Texas Red, fluoroscein- or Texas Red X-conjugated phalloidin, and AlexaFluor 488 or 594 secondary antibodies were purchased from Molecular Probes (Eugene, Oreg.).

FNf-ANP Fabrication and Characterization

Production and purification of 100 nm ANPs and GST-FNf fusion protein as well as subsequent conjugation of GST-FNf to ANPs were performed as previously described. Briefly, ANP preparations presenting increasing levels of FNf were attained by mixing increasing amounts of reactive FNf fragment (4, 40, 80, and 400 μgs) with constant amounts (400 μgs) of reactive ANPs; reactions were designated in terms of their FNf:ANP mass ratios (1:100, 1:10, 1:5, 1:1, respectively). Levels of FNf conjugated to ANPs were determined by enzyme-linked immunosorbent assay (ELISA). An ELISA for albumin was performed in parallel to normalize FNf levels. Briefly, Maxisorb 96 well plates (Nunc, Rochester, N.Y.) were coated overnight at 4° C. with known concentrations of GST-FNf (ranging from 10 μg/ml to 4 ng/ml) or albumin (ranging from 10 μg/ml to 2 ng/ml) and dilutions of each conjugation reaction. Wells were washed, blocked with 13% (W/V) non-fat dry milk in phosphate buffered saline (PBS) for 1 hour at room temperature, washed, and incubated with rabbit anti-GST (70 ng/mL) or horseradish peroxidase-conjugated rabbit anti-albumin antibody (1:2500 dilution) for 1 hour at room temperature. Wells were washed, and those incubated with anti-GST primary antibody were further reacted with horseradish peroxidase-conjugated goat anti-rabbit antibody (1:40,000 dilution) for 1 hr at room temperature. After washing, both plates were incubated with FAST OPD tablets according to the manufacturer's instructions. The color reaction was allowed to proceed for 30 minutes, and absorbance read at 450 nm in a multiwell plate reader. The levels of PNf displayed on each preparation of FNf-ANPs were calculated by linear regression using the standard curve obtained from the recombinant GST absorbances. Values for FNf conjugated to ANPs were normalized to values obtained from albumin ELISA.

Texas Red-labeled FNf-ANPs: Texas Red fluorophore (480 μg) was added to the albumin solution (30 ml reaction volume) at the final stirring step (37° C.), which is when ANPs begins to form, to incorporate Texas Red into the ANP. Non-encapsulated Texas Red was removed by dialysis. FNf were conjugated to Texas Red-labeled FNf-ANPs as described above.

Substrate Preparation

Substrates were prepared by coating surfaces overnight at 4° C. with 30 μg/ml of ANPs from each preparation (1:100, 1:10, 1:5, 1:1) of FNf-ANPs or FNf. Using the absorbance readings from the anti-GST ELISA for each FNf-ANP preparation, it was possible to use linear regression analysis to determine the bulk coating concentration of FNf required to achieve equivalent levels of adsorbed FNf as that presented on ANP. The bulk coating concentrations of GST-FNf for equivalent display were 0.5, 2.1, 3.1, and 6.0 μg/ml for the 1:100, 1:10, 1:5, and 1:1 FNf:ANP mass ratio reactions, respectively. Surfaces were washed with sterile PBS, blocked with 1% (w/v) bovine serum albumin for 1 hour at 37° C., and washed again with sterile PBS. For indicated experiments, surfaces were pre-treated with an oxygen plasma (March Plasma Inc., 5 minutes, 50 W, 670 mTorr $O_2$) prior to incubation with FNf or FNf-ANPs. We ascertained using ELISA that the cell binding domain exposure of the ligand on both passively adsorbed and plasma-treated immobilized substrates was equivalent, ensuring that plasma treatment did not markedly alter the cell accessibility of the ligand.

Cell Adhesion Assay

To quantify cell attachment to FNf-ANPs, 96-well non-tissue culture dishes were coated overnight at 4° C. with FNf-ANPs or FNf as described above. Wells were washed with PBS and blocked with 1% bovine serum albumin. After washing with PBS, HFF were plated at $2.5 \times 10^4$ cells/well and incubated for 60 minutes at 37° C. Medium and unbound cells were removed by inversion of the plate and two washes with PBS. Quantification of the number of adherent cells was performed using the hexosaminidase assay. Briefly, substrate composed of a 1:1 mixture of 0.5% Triton-X 100 and 7.5 mM β-nitrophenyl N-acetyl β-D glucosaminide in 0.1 M citrate buffer, pH 5.0, was added to each well and incubated for 90 minutes at 37° C. The reaction was terminated with 50 mM glycine/5 mM EDTA, pH 10.4 and the absorbance read at 405 nm on a multiwell plate reader.

Immunofluorescence Microscopy

Labtek chamber slides (Nalge Nunc International, Rochester, N.Y.) were coated overnight at 4° C. with FNf-ANPs or FNf as described above to attain equivalent display with FNf. Substrates were subsequently blocked with BSA and washed with PBS. Fibroblasts were seeded at densities and incubated for times described in each figure legend. After incubation at 37° C., samples were fixed with either 20 or 3.7% formaldehyde for 9 minutes or 15 minutes, respectively, and permeabilized with 0.5% Triton-X 100 for 20 minutes; only samples stained with anti-fibronectin antibody (clone IST-4) or anti-integrin β1 were fixed with 2% formaldehyde. Samples were then incubated with primary antibodies in blocking buffer (3% BSA) for 1 hour, washed, and further incubated with the appropriate secondary antibodies for 1 hour. Where indicated, cells were also incubated with TexasRed X- or fluoroscein-conjugated phalloidin to visualize F-actin. Cells were examined using a Leica SP/2 Confocal Laser Scanning Microscope.

In order to discern HFF-derived fibronectin from the FNf conjugated to ANPs or adsorbed to the substrate, an anti-fibronectin monoclonal antibody whose epitope lies outside of the $9^{th}$-$10^{th}$ type III repeat of the FNf was used to stain for fibronectin in these assays; the epitope for the monoclonal anti-fibronectin antibody is located in the $5^{th}$ type III repeat of human fibronectin.

Treatments with Y27632 and Soluble FNf-ANP and FNf

HFF were seeded on FNf-ANPs or FNf pre-coated surfaces prepared as described above. Two hours after seeding, cells were treated with Y27632 (3 μM). Cells were cultured overnight at 37° C. before being processed for immunofluorescence. For soluble FNf-ANP studies, HFF were seeded on non-coated Labtek chamber slides for 2 hours before being incubated with FNf-ANPs or FNf at concentrations used for surface adsorption as described above. Cells were cultured overnight at 37° C. in the continued presence of FNf-ANPs or FNf and processed for immunofluorescence.

Image Analysis

Two-dimensional image analysis was performed on cell specimens double-stained with Texas Red-phalloidin (red for actin) and FITC-labeled secondary antibody against cell-secreted fibronectin antibody (green for fibronectin) using Image Pro Plus, version 5.0 (Media Cybemctics, Silver Spring, Md.). To examine fibronectin fibril coverage found only in the extracellular matrix, a semi-automated method was developed to identify fibrils only found in the extracellular matrix and assess assembly. Briefly, the images were filtered, segmented and analyzed to determine the extent of fibronectin assembled in the ECM in terms of the area occupied by fibronectin fibrils. Within each actin-stained image, the upper and lower, boundaries of the red fluorescence intensity were prescribed with a view to minimize the selection of all the pixels in the field corresponding to the actin stain (red) and to maximize the pixels that corresponded to the unlabeled ECM. The fibronectin stained image (green) was then used to prescribe the upper and lower boundaries of the green fluorescence intensity so that the selection of the green corresponding to fibronectin fibrils was maximized. The intensity range values from the red and green image were then applied to discriminate the fibronectin label within the ECM space using the overlay image of actin and fibronectin staining. By simultaneously applying the obtained values for the green and red fluorescent ranges to the overlay image, only the colocalized pixels that corresponded to both fibronectin and ECM space were identified, thus excluding intracellular fibronectin. Once these objects were selected and outlined, the area of these objects was determined by Image Pro and converted to squared micrometer units based on the objective and zoom factor used during image acquisition. This process was validated through effective comparison of the extent of matrix assembly obtained via semi-automated analysis to that obtained via manual thresholding.

Statistical Analysis

Data are expressed as mean±standard deviation and represent one of two or three independent experiments performed in duplicate or triplicate. Statistical analysis was performed using one-way analysis of variance (ANOVA). If ANOVA revealed a significant difference between groups, it was followed by multiple comparison testing to determine which groups were statistically different. A p value of ≤0.05 was considered to be statistically significant.

Example 1

Surface Characterization

By maintaining the amounts of albumin nanoparticles ("ANPs", also referred to as "nanocarriers" or "ANCs") constant while increasing the amount of fibronectin fragment ("FNf") added to each conjugation reaction, four preparations of fibronectin fragment attached to the nanoparticles ("FNf-ANP") were fabricated, each displaying increasing levels of FNf. To quantify the display GST-FNf on ANPs, particles were adsorbed onto surfaces and an ELISA was performed with an anti-GST antibody; serial dilutions of GST-FNf were used to generate a standard curve.

A constant mass of reactive ANPs (400 μgs) was incubated with increasing amounts of reactive FNf (4 μgs, 1:100 reaction; 40 μgs, 1:10 reaction; 80 μgs, 1:5 reaction, and 400 μgs, 1:1 reaction) and purified by dialysis to remove unconjugated FNf. FNf-ANPs from the 4 conjugation reactions were analyzed for levels of covalently conjugated FNf expressed on the surface of ANPs by performing an ELISA for GST; values were normalized to the levels of albumin. * p≤0.05.

As the concentration of FNf added to each conjugation reaction was increased, there followed a concomitant rise in the level of FNf displayed on ANPs, ranging from 0.13 μg/cm$^2$ to 1.70 μg/cm$^2$ (FIG. 1). Immunofluorescence staining of surfaces coated with FNf-ANPs showed homogenous adsorption at all concentrations (data not shown).

Example 2

Nanoparticle Display of FNf Modulates Early Cellular Behavior

Figure 2:
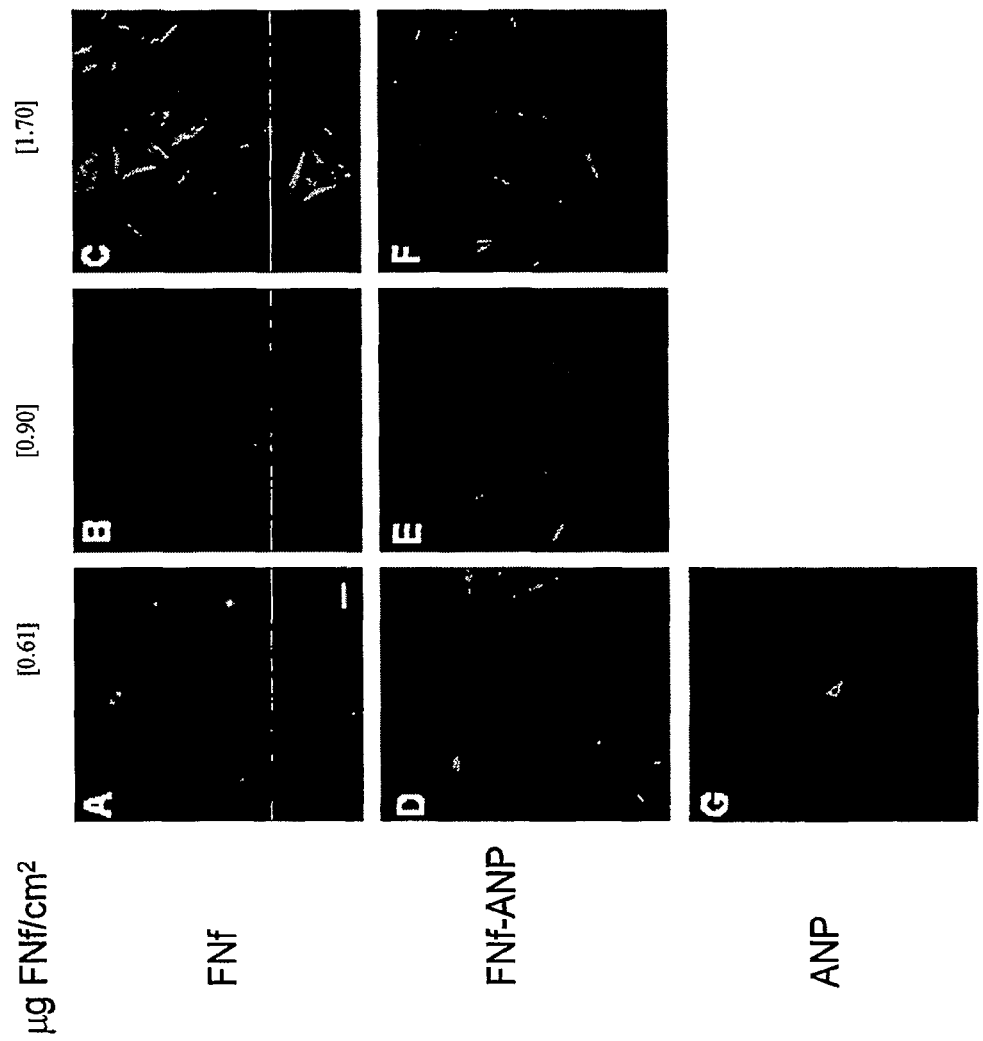
FIGS. 2A-G illustrate early cell morphogenesis in response to nanoparticle presentation of FNf (FIGS. 2A-C), FNf-ANP (FIGS. 2D-F), and ANP (FIG. 2G) at three different concentrations of FNf.

To characterize the effect of nanoparticle display of FNf on early cellular responses, adhesion and morphology were examined. Morphology examined at early time points (45 minutes post seeding) revealed that fibroblasts were well spread on FNf-ANP but minimally spread on FNf (data not shown). These trends in cell morphogenesis support the low cell attachment achieved with FNf compared to that attained with FNf-ANP. Next, we extended the culture time of human foreskin fibroblasts ("HFF") on FNf-ANPs or equivalent FNf, and evaluated cellular morphology. HFF (2.3×10$^4$ cells/ cm²) were cultured for 5 hours on surfaces prepared as described in Materials and Methods, then stained for F-actin with Texas Red X-conjugated phalloidin. Bar, 40 µm. After 5 hours of culture (FIG. 2), HFF on all concentrations of FNf showed a flattened, well-spread appearance.

However, the display of FNf on ANPs altered HFF morphology from well spread, to a stellate shape with long, slender projections. To analyze cellular morphology, shape factors were quantified for all conditions. Shape factors, defined, as (perimeter)²/(4π(area), were determined for on average 25 cells condition from random fields using Image Pro Plus Software. Shape factor establishes the degree of variance from a circle, and can vary from 1 for a perfectly circular object, to greater than 1 for a highly ruffled or elongated shape. There were statistically significant differences in cell shape factor as a result of FNf presentation via ANPs. While values for shape factor at all FNf densities remained around 4, those for FNf-ANPs ranged from 6-10, indicating that ANP display of FNf stimulated HFF to adopt an extended or stellate morphology. Selected studies were also conducted to examine early cell attachment behavior on surfaces adsorbed with each of the four FNf-ANP preparations described above or corresponding FNf alone, such that levels FNf display were equivalent between each modality of ligand display as determined by ELISA. We observed no detectable attachment at the lowest amount of ligand tested, either adsorbed to the surface or presented via ANPs. However, at all other concentrations, there was a marked increase in the number of cells attached to FNf displayed on ANPS relative to equivalent levels of FNf simply adsorbed to the surface. In addition, in the concentration range tested for FNf adsorption, there was no significant increase in cellular adhesion even at the highest concentration of FNf.

Example 3

Increased Fibronectin Matrix Deposition in Response to FNf Presentation on ANPs

Figure 3:
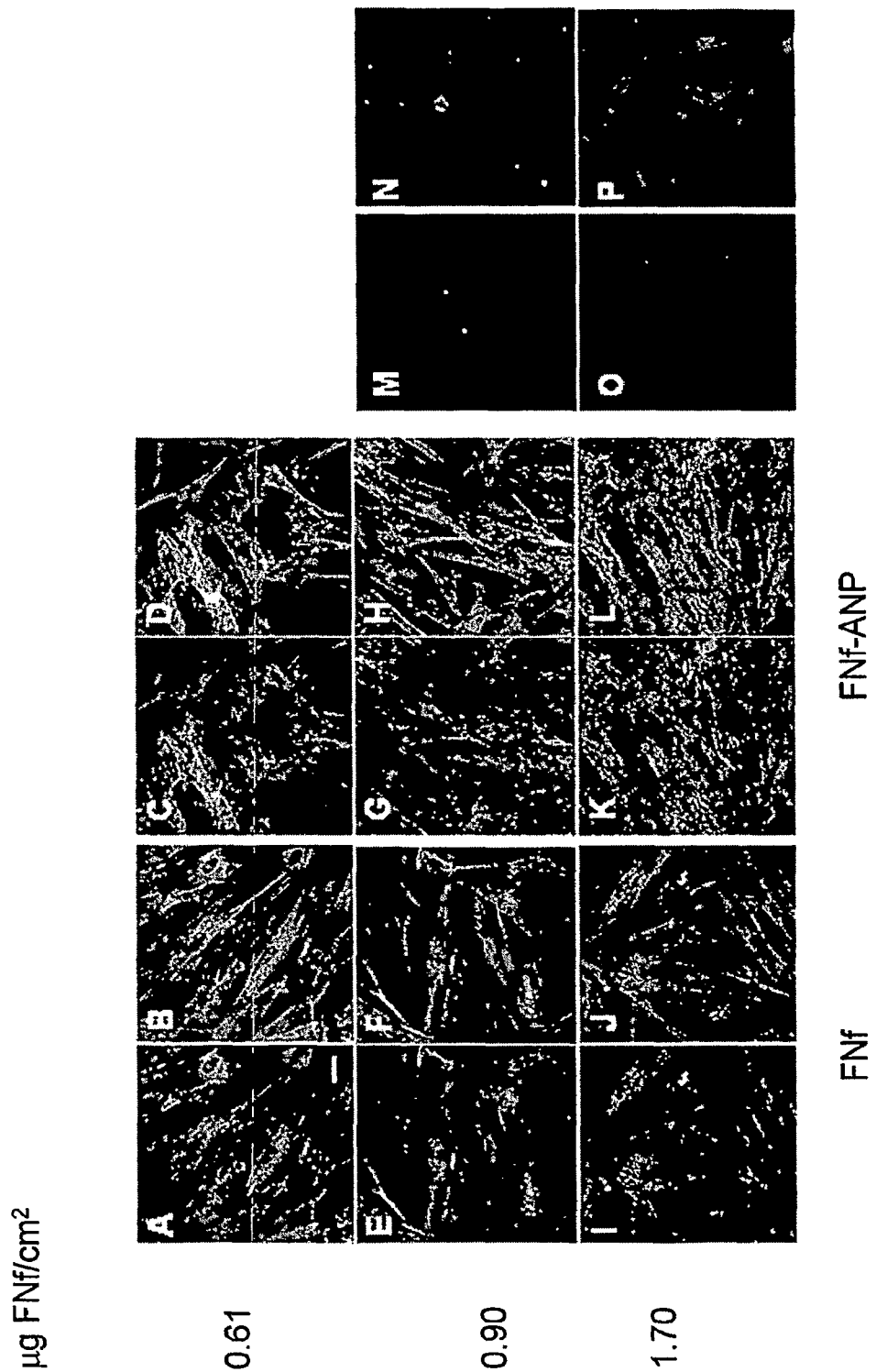
FIGS. 3A-P illustrate an enhanced deposition of fibronectin matrix fibrils by HFF in response to nanoparticle display of FNf (FIGS. 3C, D, G, H, K, and L) as compared to FNf alone (FIGS. 3A, B, E, F, I, and J).

Cell adhesion and morphology assays showed that HFF were responding differently to FNf depending on its presentation. A major function of fibroblasts is to assemble fibronectin into matrix fibrils. Therefore, the ability of FNf-ANPs to modulate ECM assembly by HFF was tested. HFF were seeded on these surfaces at $3.6\times10^4$ cells/cm². Substrates were coated FNf-ANPs (FIG. 3a, panels C, D, G, H, K, L) and FNf (FIG. 3, panels A, B, E, F, I, J) such that equivalent levels of FNf were expressed on the surface. After 24 hours, cells were fixed, permeabilized, and processed for immunofluorescence as described in Materials and Methods. Fibronectin matrix fibrils (FIG. 3, panels A, C, E, G, I, K) were visualized using a monoclonal anti-fibronectin, followed by Alexa Fluor 488-conjugated anti-mouse antibody. Cells were also stained for F-actin with Texas Red-X phalloidin. FIG. 3, panels B, D, F, H, J, and L, are overlay images of fibronectin and actin staining. Not shown for brevity are the following controls: cells on substrates coated with ANP (no fibronectin assembly detected), cells incubated with secondary antibody only and counter-stained with phalloidin (no green fluorescence detected). Bar, 20 µm.

There was no obvious difference in the matrix deposition of HFF-derived fibronectin when cells were grown on the lowest levels of FNf ligand, either substrate-adsorbed FNf (FIG. 3, panels A, E) or FNf-ANPs (FIG. 3, panels C, G). In contrast, at the highest densities of FNf, there was a dramatic increase in the assembly of fibronectin into matrix fibrils in response to FNf-ANPs (panel I vs K). Analysis of fibronectin only associated with the extracellular-matrix reveals that there is a 42% increase (p=0.004) in the surface area occupied by fibronectin matrix fibrils resulting from culture on FNf-ANPs versus that elicited from an equivalent density of surface adsorbed FNf. Comparing data attained from both the semi-automated and manual identification approaches revealed similar levels of extracellular fibronectin fibrils (data not shown), thus validating the accuracy of the semi-automated quantification of matrix formation.

Example 4

Figure 4:
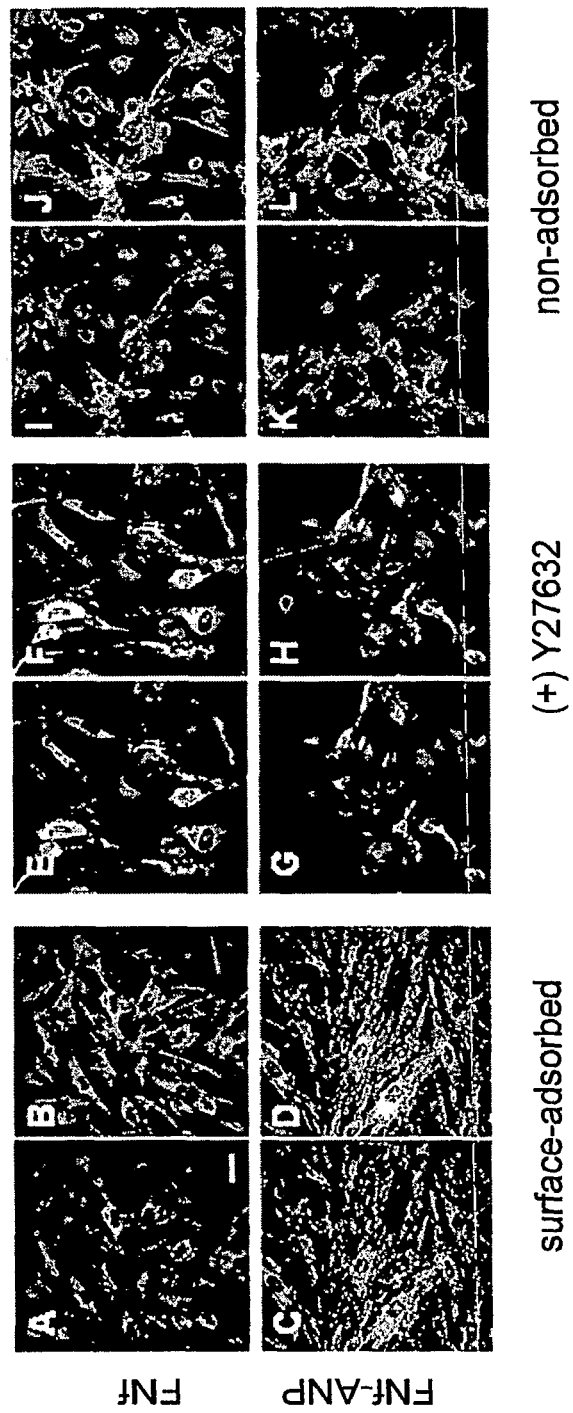
FIGS. 4A-L illustrate that increased fibronectin matrix assembly requires RhoA-dependent contractility in addition to receptor ligation, where HFF were (i) seeded on bare coverglass (FIGS. 4I, J, K, and L), substrates adsorbed with either ligand alone (FIGS. 4A, B, E, and F) or ligand conjugated to ANP (FIGS. 4C, D, G, and H) and (ii) treated with 3 μMY27632 (FIGS. 4E, F, G, and H), FNf (FIGS. 4I and J), or FNf-ANP (FIGS. 4K and L).

Receptor Ligation is not Sufficient for FNf-ANP Mediated Induction of HFF-Derived Fibronectin Matrix Deposition To begin elucidating mechanisms by which FNf-ANPs activated the incorporation of fibronectin into the ECM, we probed whether FNf-ANP receptor ligation was sufficient for matrix deposition in the absence of any physical forces afforded by adsorption to the substrate. HFF ($3.6\times10^4$ cells/cm²) were seeded on bare coverglass (FIG. 4, panels I, J, K, L) or substrates adsorbed with the highest concentration of FNf [1.70 µg/cm²], either ligand alone (FIG. 4, panel A, B, E, F) or conjugated to ANP (FIG. 4, panel C, D, G, H). Cells were processed for immunofluorescence. Panels B, D, F, H, and J, L are overlay images of fibronectin and actin staining. HFF were seeded on coverglass, then incubated with media containing FNf-ANPs (FIG. 4, panel K, L) or equivalent amounts of FNf (FIG. 4, panel I, J). Compared to FNf-ANP that were surface adsorbed (FIG. 4a, panel C, D), presentation of FNf, whether alone or conjugated to ANPs, via the culture medium was not sufficient to elicit cellular responses culminating in increased deposition of fibronectin into the ECM. Analysis of matrix incorporation of HFF-derived fibronectin showed that there were significantly fewer extracellular fibrils of fibronectin when FNf-ANPs were presented to cells in the media compared to substrate presentation.

Example 5

FNf-ANP Enhanced Fibronectin Deposition into the ECM Requires RhoA Signaling

The small GTPase, RhoA, mediates fibronectin incorporation into the ECM as it regulates cellular contractility or tension which is thought to expose cryptic self-assembly sites within the fibronectin molecule that allow for matrix assembly. Zhong et al., *J Cell Biol* 141 (2): 539 (1998); Landergen et al, *J Immunol Methods* 67 (2): 379 (1984); Hocking et al, *J Cell Biol* 133 (2): 431 (1996). Since cellular contractility depends on attachment to substrates, we determined whether inhibition of cellular contractility modulated the induction of fibronectin matrix deposition by substrate-adsorbed FNf-ANP. After 2 hours, cells were treated with 3 µm Y27632 (FIG. 4, panel E, F, G, H), FNf (panel I, J), or FNf-ANP (panel K, L). Addition of the Rho kinase inhibitor Y27632 to HFF abrogated FNf-ANP induced matrix assembly by HFF (FIG. 4, panels G vs. C). Analysis of fibronectin matrix assembly demonstrated significantly decreased levels of fibronectin matrix fibrils in the extracellular space of HFF cultured on FNf-ANP and treated with Y27632, compared to control conditions.

Example 6

Surface Immobilization of FNf-ANP Inhibits β1 Translocation and Fibronectin Matrix Assembly The α5β1 integrin transmits cytoskeleton-generated tension to the extracellular fibronectin molecules via a specific local pattern of integrin movement. Pankov et al, *J Cell Biol* 148 (5): 1075 (2000). To determine whether presentation of FNf via ANPs promotes fibronectin matrix assembly by regulating the dynamics of β1 integrins, a time course of the localization of ligand-occupied β1 on FNf and FNf-ANP was performed. A cation and ligand-induced binding site (CLIBS) class of monoclonal antibody (clone 12G10), that recognizes an extracellular epitope expressed after ligand occupation of human β1 integrin receptors was employed.

Figure 5A:
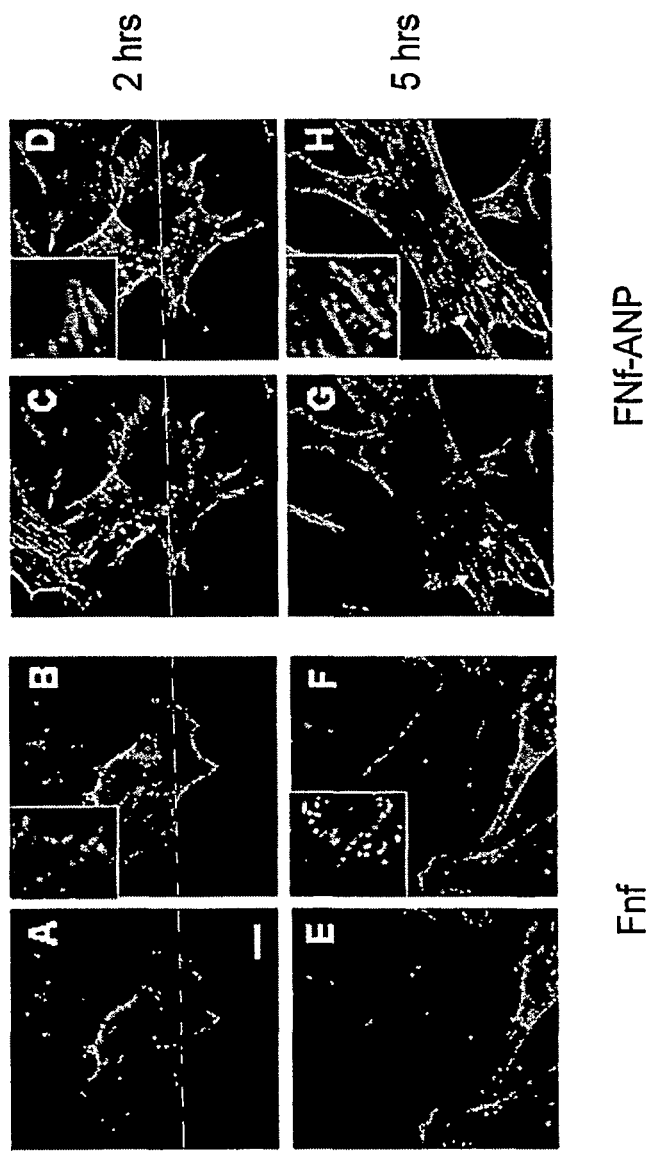
FIGS. 5aA-5e illustrate that enhanced β1 recruitment on FNf-ANP induces fibronectin fibrillogenesis, where (i) FIGS. 5aA-5aH illustrate the results of an experiment wherein HFF were seeded on FNf (FIGS. 5aA, B, E, and F) or FNf-ANP (FIGS. 5aC, D, G, and H); (ii) FIGS. 5bA-5bD illustrate the results of an experiment wherein HFF were seeded on surfaces treated with oxygen plasma prior to coating with FNf (FIGS. 5bA and B) or FNf-ANP (FIGS. 5bC and D); (iii) FIGS. 5cA-5cF illustrate the results of an experiment wherein HFF were seeded on Texas Red-labeled FNf-ANP and stained for F-actin (panel B and E) with fluorescein-phalloidin, with images showing Texas Red (panels A and D), fluorescein-phalloidin (panels D and E), and overlay (panels C and F); (iv) FIGS. 5dA-5dH illustrate the results of an experiment wherein HFF were seeded on FNf (panels A, B, E, and F) or FNf-ANP (panels C, D, G, and H), some of which were pre-treated with oxygen plasma prior to coating with FNf or FNf-ANP (panels E, F, G, and H); and (v)

FIG. 5a illustrates the results of an experiment wherein HFF ($2.7 \times 10^4$ cells/cm$^2$) were seeded on the highest concentration [$1.70 \, \mu g/cm^2$] of FNf or FNf-ANP and fixed after 2 and 5 hours. Cells were stained with a monoclonal anti-active 131 antibody (clone 12G 10), followed by Alexa Fluor 488-conjugated anti-mouse IgG. F-actin was visualized by staining with Texas Red-X phalloidin. Panels B, D, F, H, are overlay images of 131 and actin staining. Arrows denote translocating β1. Bar, 20 μm.

Figure 5B:
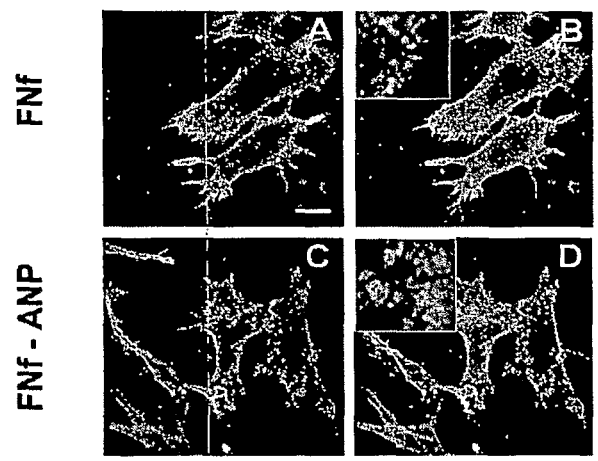
FIG. 5e is an analysis of fibronectin matrix deposition.

In an experiment illustrated by FIG. 5b, surfaces in panels A-D were treated with oxygen plasma prior to coating with the highest concentration of FNf or FNf-ANP. HFF were seeded, fixed, and stained as described above. Bar, 20 μm.

Figure 5C:
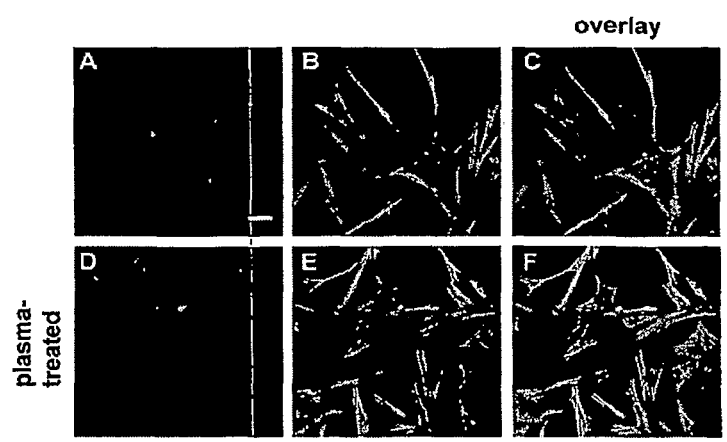

In an experiment illustrated by FIG. 5c HFF were seeded on Texas Red-labeled FNf-ANP [$1.70 \, \mu g/cm^2$] and after 24 hours, fixed and stained for F-actin (panel B and E) with fluorescein-phalloidin. Panels A and D depict Texas Red FNf-ANP, and panels C and F are overlay images of labeled FNf-ANP and actin staining. Bar, 40

Figure 5D:
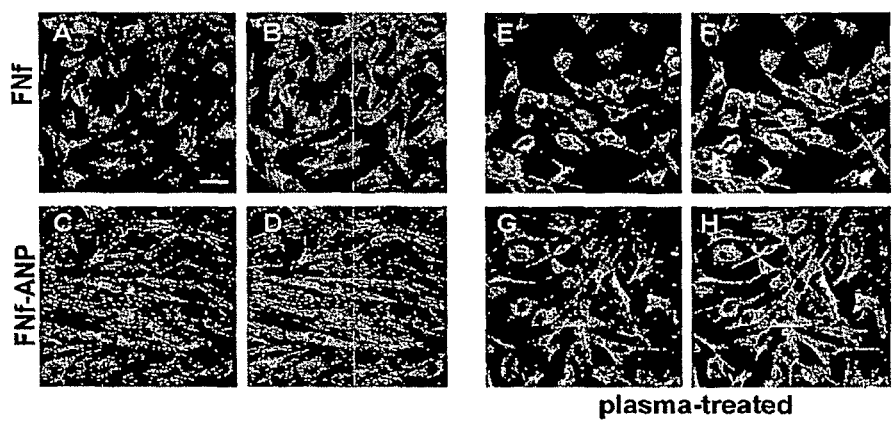
Figure 5E:
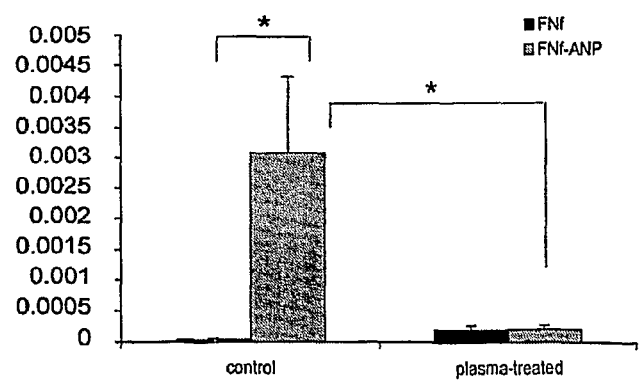

FIG. 5d illustrates the results of an experiment, wherein HFF were seeded on the highest concentration [$1.70 \, \mu g/cm^2$] of FNf (panels A, B, E, F) or FNf-ANP (panels C, D, G, H); panels E, F, G, H were pre-treated with oxygen plasma prior to coating with FNf or FNf-ANP. Cells were processed for immunofluorescence as described in FIG. 3. Panels B, D, F, H are overlay images of fibronectin and actin staining. Bar 20 μm. Finally, FIG. 5e is an analysis of fibronectin matrix deposition. * $p \leq 0.05$.

Two hours after plating, focal contacts on FNf-ANP surfaces are more enriched in ligand-occupied β1 than on equivalent densities of adsorbed FNf (FIG. 5a, inset of panel D vs B), suggesting that the presentation of FNf on ANPs enhanced the recruitment of β1 to focal contacts. By 5 hours of culture, the concentration of ligand-occupied β1 integrins remained higher on FNf-ANPs than on FNf alone. In addition, integrin staining extended along bundles of actin filaments on FNf-ANP suggesting that β1 integrin complexes might have translocated away from the cell periphery. Treatment of surfaces with plasma, an electronically neutral mixture of electrons, ions, and radicals, creates chemically active functional groups on surfaces to increase the interaction of protein with the surface therefore making it possible to functionally immobilize proteins on surfaces without compromising bioactivity. Liston, *J Adhesion* 30:199 (1989); Schmalenberg, *Biomaterials* 25 (10): 1851 (2004). Pre-treatment of surfaces with oxygen plasma prior to adsorption of FNf-ANPs resulted in a loss of linear organization of β1 along actin filaments (compare FIG. 5a, panels G, H to 5B, panels C, D). Although there appeared to be more staining for β1 on plasma-treated surfaces, 131 distribution was quite punctuate and not organized along actin filaments as observed on non-plasma treated FNf-ANP (FIG. 5b). These observations suggested that oxygen plasma treatment blocked the rearrangement of 131.

Oxygen plasma treatment was therefore used to determine if cells mobilized FNf-ANPs, and whether this movement was critical to FNf-ANP-induced fibrillogenesis. Cell-associated, as well as extracellular, aggregates of FNf-ANP were detected on non-plasma treated surfaces, indicating that cells are actively clustering and mobilizing FNf-ANP (FIG. 5c, panels A, C); similar aggregation was not detected in the absence of cells (data not shown). Plasma-treatment of surfaces decreased the overall amount of FNf-ANP aggregation (FIG. 5c, panels D, F) suggesting that cells were restricted in their ability to mobilize FNf-ANP. To determine if reduction of FNf-ANP mobility and β1 translocation were associated with a decrease of fibronectin matrix deposition, fibronectin fibrillogenesis was assayed. The immobilization of FNf-ANP (FIG. 5d, panel G) compared with non-immobilized FNf-ANP surfaces (FIG. 5d, panel C) inhibited fibronectin matrix assembly. Analysis of fibrillogenesis demonstrated significantly decreased levels (p=0.0002) of fibronectin matrix fibrils in the extracellular space of immobilized versus non-immobilized FNf-ANP surfaces (FIG. 5e).

The following description of materials and methods is applicable to the rest of the examples below (Examples 7-11).
Preparation, Purification, and Characterization of Albumin Nanocarriers (ANC)

Albumin derived nanocarriers were fabricated and functionalized as described above. Human serum albumin [30% (w/v)] (Sigma, St. Louis, Mo.) was diluted to 1% with phosphate-buffered saline (PBS) and passed through a 0.22 μm filter (Fisher) to remove potential aggregates of albumin. The pH of the albumin solution was raised to 10.65 with 0.1 N NaOH and heated to 80° C. for 10 minutes. After cooling to 25° C. in an ice bath, the solution was kept at room temperature for 10 minutes, and the pH lowered to 6.04 with 0.1N HCl. The albumin solution was heated to 37° C. and stirred to allow the self-assembly of albumin chains through intermolecular disulfide bonding. Further reaction and aggregation were stopped by deactivating the remaining thiol groups by incubation with 0.1% (w/v) iodoacetamide (Sigma) for 1 hour at room temperature. Monomeric albumin (66 kDa) was removed from the preparation by dialysis (MWCO 100 kDa) against PBS. The buffer was changed twice after two hours before final dialysis at 4° C. overnight. After recovery from dialysis, albumin aggregates larger than 200 nm were removed from nanocarrier preparations by passage through a 0.2 μm filter. To characterize the kinetics of formation, samples were taken after 5, 10, 15, and 20 minutes of stirring at 37° C. and analyzed by dynamic light scattering and atomic force microscopy. A PSS Nicomp 380 (Santa Barbara, Calif.) submicron particle sizer instrument with an argon ion laser at 532 nm was used for dynamic light scattering analysis.
Recombinant Protein Production and Purification Fibronectin cDNA encoding the repeats III$_9$ and III$_{10}$ were cloned into a pGEX vector for expression as a glutathione-S-transferase (GST) fusion protein. *Escherichia coli* cells were transformed with the GST-FNIII$_{9-10}$ construct and fusion proteins separated from bacterial lysates by glutathione-sepharose affinity chromatography (GE Healthcare, Piscataway, N.J.) following the manufacturer's recommendations. Purity of the preparations were confirmed by loading 5 pg of pre-dialysis and post-dialysis ANC suspensions and monomeric albumin in a 10% precast Criterion gel (Biorad). GST-FNIII$_{9-10}$ fragments were stored at −20° C. and thawed immediately before use.
Preparation of Ligand-Conjugated Albumin Nanocarriers Conjugation of the GST-FNIII$_{9-10}$ fragment to the ANC was accomplished using the heterobifunctional cross-linking reagent, N-succinimidyl 3-(2-pyridyldithio)propionate (SPDP) (Sigma) and conventional peptide chemistry techniques. Briefly, SPDP reacts with the amine groups to form an amide linkage, while the 2-pyridyldithiol (PD) group at the other end can react with sulfhydryl residues to form a disulfide linkage. GST-FNIII$_{9-10}$ fragment and the various sized ANCs and monomeric albumin (1 mg and 2 mg, respectively) were both separately reacted with SPDP at a final concentration of 500 µM for 30 minutes at room temperature. The by-products of the reaction were removed by dialysis (MWCO 6 kDa) against PBS. Next, dithiothreitol (DTT) at a concentration of 0.5 mg DTT per mg of modified GST-FNIII$_{9-10}$ fragment was added to the recombinant fragment to release the PD leaving and form the free sulfhydryl group. The thiolated ligand (ligand-SH) was purified from excess DTT by dialysis (MWCO 6 kDa). Total protein recovered from dialysis was quantified for both the ANC and the GST-FNIII$_{9-10}$ fragment by BCA protein assay (Pierce, Rockford, Ill.). Finally, 100 µg of reactive nanocarrier of various sizes (30, 50, 100, and 125 nm ANC-PD or albumin-PD) and varying mass of ligand-SH (1, 10, or 100 µg) were incubated together at room temperature for 6 hours to conjugate the GST-GST-FNIII$_{9-10}$ fragment to the surface of the carrier. Excess GST-GST-FNIII$_{9-10}$ fragment not consumed in the conjugation reaction was removed from the conjugation products by dialysis (MWCO 100 kDa) against PBS.

Interfacial Characterization of GST-FNIII$_{9-10}$-ANC Adsorbed on Substrates

Levels of GST-FNIII$_{9-10}$ conjugated to ANC were determined by enzyme-linked immunosorbent assay (ELISA). An ELISA for albumin was performed simultaneously for normalization of GST-FNIII$_{9-10}$ levels. Briefly, GST-FNIII$_{9-10}$-ANC and standards of recombinant GST (Upstate, Lake Placid, N.Y.) or albumin (Sigma) were adsorbed onto coverglass bottom 96 well plates (Nunc) overnight at 4° C. Recombinant GST standards were made by diluting stock rGST (1 mg/ml) to 10 µg/ml with PBS and serially diluting with PBS. At the same time, GST-FNIII$_{9-10}$ at 4 mg/ml was serially diluted with one part GST-FNIII$_{9-10}$ and one part PBS, and these various dilutions were adsorbed onto the well plates.

Albumin standards were made by serially diluting stock albumin (300 mg/ml) with PBS. Wells were washed three times with PBS to remove unbound ligand and incubated with blocking buffer (1×PBS, 3% non-fat dry-milk) for 1 hour at 37° C. After washing three, times with PBS, substrates were incubated with rabbit anti-GST (70 ng/mL) (Sigma) or horseradish peroxidase-conjugated rabbit anti-albumin (1:2500 dilution) (MP Biomedicals, Irvine, Calif.) for 1 hour at 37° C. Wells incubated with anti-GST primary antibody were washed and further reacted with an appropriate horseradish peroxidase-conjugated goat anti-rabbit antibody (1:40,000) (Sigma) for 1 hour at 37° C. Sigma-FAST OPD tablets (Sigma) were used according to manufacturer's protocol as a substrate for the detection of peroxidase activity. The color reaction was developed for 30 minutes and absorbance read at 450 nm on a multiwell plate reader. The absorbance reading of the GST-FNIII$_{9-10}$ was used to calculate the concentration of GST-FNIII$_{9-10}$ required to get an equivalent level of GST-FNIII$_{9-10}$ adsorbed using linear regression with the standard curve of GST-FNIII$_{9-10}$ absorbances. The levels of GST-FNIII$_{9-10}$ conjugated to ANC were obtained by linear regression utilizing standard curve of rGST absorbances. Values for GST-FNIII$_{9-10}$ conjugated to the nanocarrier were normalized to albumin. To examine the role of mobility of our ligand through differential presentation, ligand and ligand-nanocarrier were immobilized to the surface using oxygen plasma pretreatment (March Plasma Inc, 60 seconds, 50 W, 670 mTorr oxygen) before ligand and ligand-nanocarrier deposition. Isotherms were established as described above.

ELISAs were also conducted to examine exposure of GST-FNIII$_{9-10}$ cell binding domains as a function of ligand nanodisplay for both passively adsorbed and immobilized substrates. Equivalent amounts of GST-FNIII$_{9-10}$ derived from GST ELISA isotherms were adsorbed on maxisorp 96 well plates overnight at 4° C. The surfaces were washed and blocked for 1 hour at 37° C. Substrates were washed again and incubated with the primary antibody specific for the cell binding domain in fibronectin (Clone 3E3; Chemicon International, Temecula, Calif.) for one hour, followed by one hour incubation with horseradish peroxidase conjugated-goat anti-mouse IgG (Sigma). Peroxidase activity was detected as described above.

Cell Culture

Human foreskin fibroblasts, HFF, a kind gift from Dr. Simpson-Haidaris, University of Rochester, Rochester, N.Y.) were cultured in McCoy's 5A Media (Invitrogen, Chicago, Ill.) supplemented with 1% Pen/Strep (Biowhittaker), 2 mM L-glutamine (Invitrogen) and 10% fetal bovine serum. For all assays, fibroblasts were washed with PBS and media was replaced with serum-free media supplemented with the above additives.

Imaging and Semi-Quantitative Analysis of Fibronectin Matrix Assembly

Matrix assembly was analyzed as a function of ligand carrier size and ligand density. Substrates with equal levels of ligand but differential presentation were adsorbed in 8-well Labtek chamber slides overnight at 4° C. Substrates were then washed generously with PBS and blocked with BSA for 1 hour at 37° C. Fibroblasts were serum-starved at least 12 hours prior to trypsinization and re-plated at a density of 35,000 cells per well in serum free media. Cells were then cultured for 24 hours at 37° C. After 24 hour incubation, media was removed and substrates were washed with DPBS with calcium and magnesium. Cells were fixed with 1% formaldehyde for 9 minutes and washed with DPBS with calcium and magnesium. Cells were permeabilized with Triton-X 100 for 15 minutes and washed with DPBS with calcium and magnesium and blocked with 1% BSA for 1 hour at 37° C. Substrates were washed and primary antibody IST-4 (Sigma) for fibronectin that binds to the 5th type III repeat of human plasma fibronectin was incubated at a 1:100 dilution in PBS overnight at 4° C. Substrates were washed and incubated with FITC-conjugated donkey anti-mouse IgG (Jackson Immunolabs, West Grove, Pa.) at a 1:200 dilution for 30 minutes at room temperature, and were then washed and incubated with Texas-red phalloidin (Molecular Probes, Eugene, Oreg.) for 20 minutes at room temperature. Substrates were washed and stored at 4° C. until image acquisition. Images were acquired using a Leica TCS SP/2 confocal microscope with a 63× objective, zoom 1.

For conditions eliciting the highest levels of matrix assembly, substrates were plasma treated with 60% oxygen and 670 mTorr pressure with a plasma generator (March Plasma Systems) and ligand was immediately deposited on treated substrates. The effect of media presentation of ligand, as opposed to surface-adsorbed ligand, was examined by seeding cells on Labtek chamber slides for 2 hours, and then adding ligand-ANC to the media. Cells were then cultured for 24 hours at 37° C. The effect of serum on matrix assembly for certain conditions was examined by culturing cells on substrates as described above without serum deprivation. As a control, whole length mouse fibronectin (Innovative Research, Southfield, Mich.) was adsorbed at 10 lag/ml overnight at 4° C., and fibroblasts were seeded in serum-free media.

Quantitation of Fibronectin Matrix Assembly

The extent of assembly of cell-derived fibronectin matrix was quantified by ELISA. Substrate conditions where the most amount of matrix assembly was visualized after 24 hours in culture were prepared as described above, along with the corresponding immobilized substrate conditions and unfunctionalized carriers. At the same time, a standard curve of whole length fibronectin, ranging from 10 μg/ml diluted 10 times with PBS was adsorbed in triplicate. Cells were deposited on substrates for 24 hours at 37° C. and washed three times at the end of the incubation period. Cells were lysed as previously described using lysis buffer composed of 8 mM $Na_2HPO_4$ at pH 9.6 and 1% NP-40 for 15 minutes at 37° C. The solution was then removed and replaced with fresh lysis buffer and the incubation continued for an additional 60 minutes. Substrates were then washed and an ELISA was performed by blocking substrates and the standard curve with 1% BSA for 1 hour at 37° C. and washing it three times. Next, the primary antibody (IST-4) at a concentration of 1:1,000, was incubated at 37° C. for 1 hour and washed off, followed by incubation of the secondary antibody, goat anti-mouse conjugated with horseradish peroxidase at a concentration of 1:10,000 (Sigma) for 1 hour at 37° C. Sigma-FAST OPD tablets (Sigma) were used according to manufacturer's protocol as a substrate for the detection of peroxidase activity. The color reaction was developed for 30 minutes and absorbance read at 450 nm on a multiwell plate reader. The absorbance reading of the fibronectin standard curve (similarly based on the IST-4 binding activity) was used to determine an equivalent bulk concentration level of fibronectin assembled.

Cell Attachment

To quantify cell attachment to ligand-ANC, 96-well non-tissue culture dishes were passively coated overnight at 4° C. with varying ligand density and presentation as described above. Wells were washed with PBS and blocked with 1% bovine serum albumin. After washing, fibroblasts were seeded at 25,000 cells/well and incubated for 1 hour at 37° C. Substrates were washed with PBS to remove unbound cells. Adhered cells were quantified using the hexosaminidase assay. Briefly, a substrate mixture composed of 1 part 0.50 Triton-X 100 and 1 part 7.5 mM [3-nitrophenyl N-acetyl [3-D glucosaminide (Sigma) in 0.1 M citrate buffer (pH 5.0), was added to each well and incubated for 90 minutes at 37° C. The reaction was terminated with a mixture of 50 mM glycine (Sigma) and 5 mM EDTA (Sigma) (pH 10.4). The absorbance was read at 405 nm on a multiwell plate reader.

Cell Morphology

Cell morphology was examined as a function of differential ligand presentation and nanocarrier size at two time points. Passively adsorbed substrates were prepared as described above. Fibroblasts that were serum deprived at least 12 hours before hand were seeded in serum free media for 1 or 5 hours at 37° C. Substrates were washed after the designated incubation time, and fixed with 3.7% formaldehyde for 15 minutes at room temperature. Substrates were washed again and permeabilized with Triton-X 100 for 15 minutes at room temperature. Substrates were washed, blocked with 1% BSA for 15 minutes at room temperature, washed again, and stained with FITC phalloidin (Molecular Probes) for 20 minutes. Substrates were washed and stored at 4° C. until image acquisition. Images were acquired with a Leica TCS SP/2 at 63×.

Displacement of Fnf-ANC During Fibroblast Contraction

The movement of ligand-ANCs was tracked by encapsulating a fluorescent probe within the ANCs. Briefly, albumin was denatured as described above. Before the solution was stirred, 10 μg of Alexa Fluor 488 (Molecular Probes) were added to the solution. The solution was then stirred to create nanocarriers and processed as described above. Various sized functionalized nanocarriers were adsorbed onto substrates such that the fluorescently labeled nanocarriers were diluted 1:1000 with unlabeled functionalized nanocarriers. Substrates were then washed and fibroblasts seeded at 2800 cells/$cm^2$. Cells were incubated for 1 hour at 37° C. and image acquisition was performed on a Carl Zeiss LSM410 microscope every 45 minutes. At each time point, a fluorescent image and a phase contrast image were acquired. Images were merged, and the distance traveled was calculated by tracking the mobile nanocarriers over 6 hours of image acquisition. Only carriers that were located at the edge of the cell at the initial time lapse sequence were tracked. For each experiment and condition, at least 15 carriers were tracked.

Quantitation of Force Curves Between Cells and Ligand-ANC Substrates

The force of interaction between cells and ligand-ANCs was evaluated using atomic force microscopy operating in fluid immersion mode. Silicon nitride cantilevers (Veeco Metrology, Santa Barbara, Calif.) were incubated overnight at 4° C. with the appropriate ligand-ANC solutions. Functionalized cantilevers were then washed with PBS and blocked with 1% BSA for 1 hour at 37° C. and washed again with PBS. Fibroblasts were seeded at a density of 2800 cells/$cm^2$ onto clean glass slides and incubated for 1 hr at 37° C. in serum free media. The ligand-adsorbed cantilever tip was allowed to carefully approach the surface of individual fibroblasts while maintaining a constant force of 0.38 N/m using an atomic force microscope (Digital Instruments Nanoscope IIIa, Santa Barbara, Calif.) under tapping mode. A force curve between the ligand-ANC adsorbed cantilever and the cell was generated by oscillating the tip at 1 Hz. As the tip oscillates, the cantilever-deflection from the photodiode is monitored, generating a force curve between the ligand-ANC-adsorbed cantilever tip and a single cell on the glass slide. The force curve is a plot of the cantilever deflection signal as a function of the voltage applied to the piezo tube. The force was calculated by the formula F=kx where k is the force constant of the spring and x is the distance from the control point in nanometers. Each condition was examined in triplicate, and for each condition force curves were generated between three to five different cells.

Example 7

Characterization of the Nanosubstrates (Albumin Nanocarriers)

Four different sized albumin nanocarriers (ANCs) were synthesized by adjusting the mixing time during self-assembly. By varying the amount of ligand reacted with a fixed mass of nanocarriers, the ligand density could be varied on different sized nanocarriers, which was measured by an ELISA performed against GST on the ligand. Interestingly, the size of the nanocarrier did not affect the density of ligand on the surface of the well plate, and the density depends on the initial amount of ligand reacted with the nanocarrier. These ligand adsorption isotherms were normalized against albumin isotherms. ELISAs for cell binding domain exposure indicated that exposure did not increase on different sized carriers.

Example 8

Matrix Assembly

Matrix assembly as a function of ligand density and presentation was first examined with immunofluorescence techniques. A serum free system was used to eliminate variables that could promote matrix assembly. Human foreskin fibroblasts were serum-starved overnight and seeded on substrates with ligand at 2.2 μg/$cm^2$ for 24 hours or 48 hours. Matrix fibrils were visualized using a monoclonal mouse anti-human fibronectin that binds to an epitope located within domain 5 of the type III repeats of human plasma fibronectin, followed by FITC-conjugated donkey anti-mouse antibody. Cells were also stained for F-actin with Texas Red phalloidin. Increased culture time allowed cells seeded on smaller-sized carriers to elongate and contract, but matrix assembly still did not commence, while larger-sized carriers not only assembled more matrix but became contracted.

At the highest ligand density examined, there was an increase in assembled fibronectin fibrils in the extracellular matrix on the larger-sized nanocarriers (100 and 125 nm) compared to the smaller-sized nanocarriers (30 and 50 nm) and ligand adsorbed substrate. Human foreskin fibroblasts were serum-starved overnight and seeded on substrates with ligand at 2.2 µg/cm$^2$ for 24 hours or 48 hours. Matrix fibrils were visualized using a monoclonal mouse anti-human fibronectin that binds to an epitope located within domain 5 of the type III repeats of human plasma fibronectin, followed by FITC-conjugated donkey anti-mouse antibody. Cells were also stained for F-actin with Texas Red phalloidin.

At lower ligand densities, there was no detectable assembly of matrix regardless of ligand presentation. Fibrils were not seen in unfunctionalized ANCs (negative control conditions) nor on control substrates adsorbed with whole length mouse fibronectin. We examined whether ligation of integrins to ligand-ANCs was sufficient to induce matrix assembly by supplementing the media with ligand-ANC, as opposed to adsorbing the ligand-ANC directly to the well, and matrix assembly was not evident. The addition of serum to the culture medium induced matrix assembly on substrates that did not previously demonstrate assembly in the serum-free conditions. An increase in the culture time to 48 hours resulted in increased elongation of cells on smaller-sized carriers, but matrix assembly was still not observed. On larger-sized carriers, more prominent fibronectin matrix fibrils were visualized after 48 hrs.

The extent of matrix assembly was quantified using ELISA techniques. Cells were cultured on substrates as described in the text and lysed to leave behind the assembled matrix. Values were derived by back-calculating the concentration based on the standard curve of whole length fibronectin. Quantifying matrix assembly using immunochemistry techniques on the assembled matrix by cells after 24 hours in culture at the highest ligand loading compared to unfunctionalized carriers, indicated a distinguishable difference in fibronectin assembled between different sized carriers at the highest ligand loading (FIG. 6). This analysis revealed a 22% increase of fibronectin matrix assembled. Negligible amounts of fibronectin were assembled by fibroblasts cultured on smaller-sized carriers (30 and 50 nm) and unfunctionalized carriers.

Example 9

Cell Attachment and Morphology

Figure 7A:
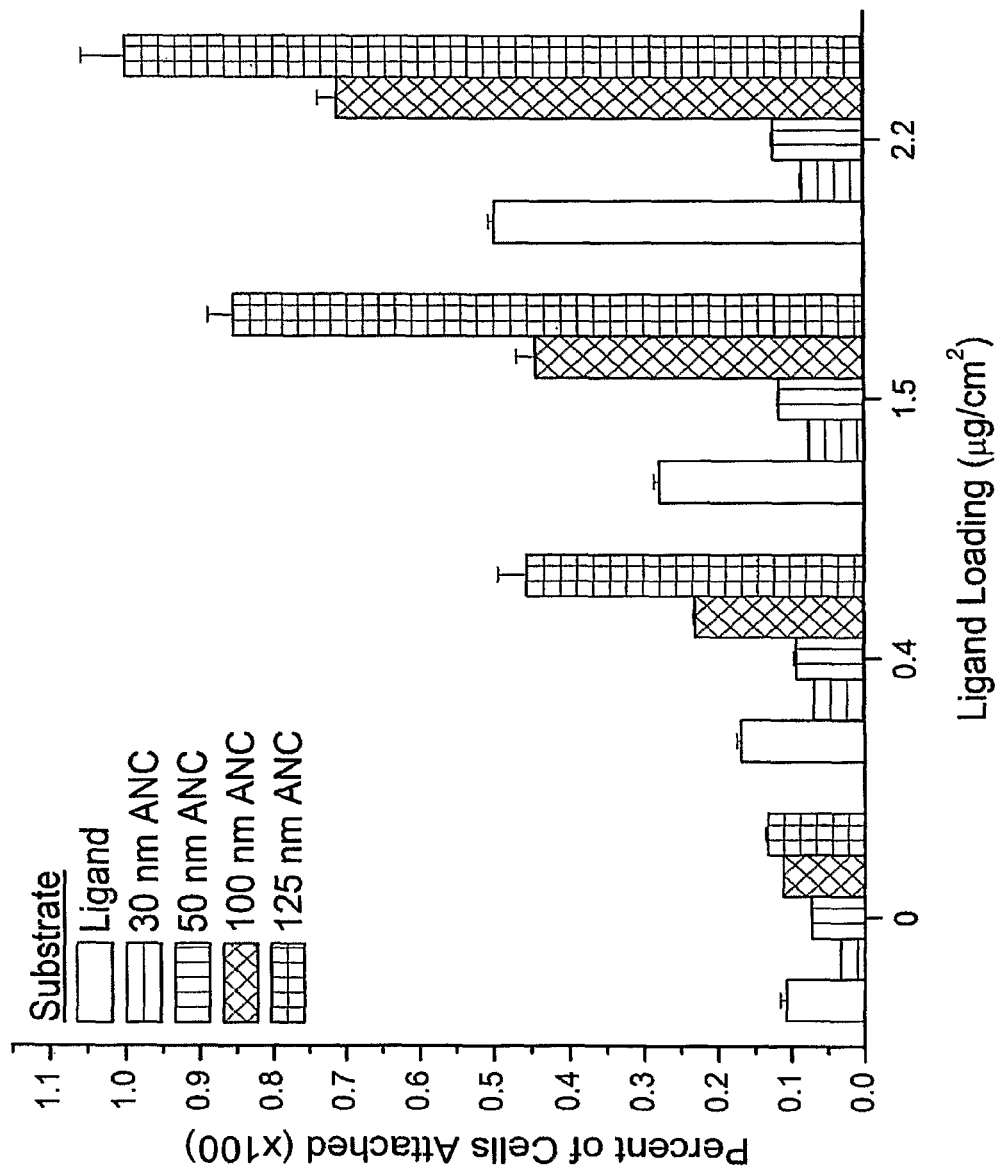
FIGS. 7A and B illustrate cell adhesion to ANCs of different sizes.

Cell attachment is one of the earliest cell anchorage responses to substrates. To examine if the nanoscale presentation of ligand could alter early cell binding and attachment events, fibroblasts were seeded on ligand-adsorbed substrates of three different ligand densities with different presentations (FIG. 7a). In this experimental setting, equal numbers of cells were seeded on surfaces with equal amounts of fibronectin fragment that was differentially presented to the cells as either ligand adsorbed or via various sized ANCs. Cells were incubated for 1 hour, unbound cells were washed, and the number of adherent cells was quantified using the hexosaminidase assay. The number of cells attached to each surface is normalized to the condition with the highest attachment (2.2 µg/cm$^2$ on 125 nm Fnf-ANC).

Attachment increased with increased ligand density. For a specific ligand density, the highest degree of attachment was seen on the largest sized nanocarrier (125 nm), with significant attachment, but to a lesser degree, on the 100 nm sized nanocarrier and ligand adsorbed substrate, both distinguishable from each other when analyzed by ANOVA. On 30 and 50 nm sized carriers, attachment was much less and not distinct from each other.

Figure 7B:
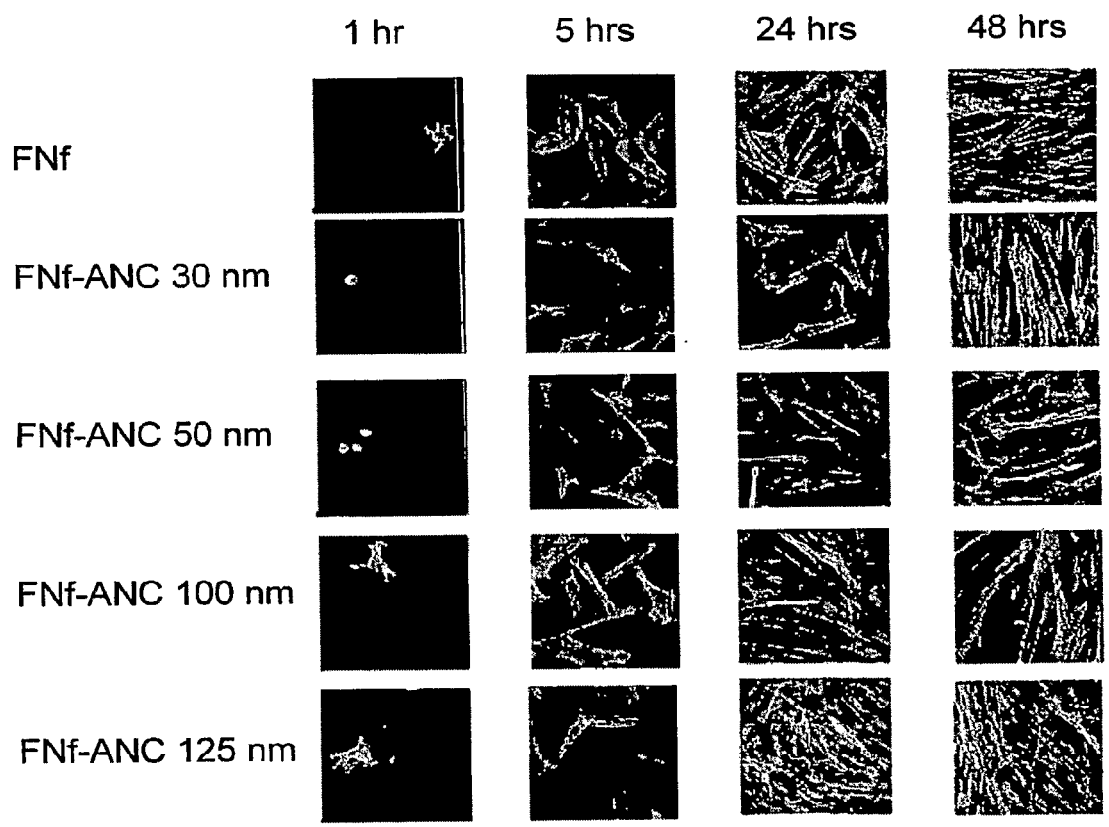

The effects of ligand presentation on cytoskeletal morphology were examined by labeling F-actin at two different time points (FIG. 7b). In that experiment, cell morphology was examined of fibroblasts cultured at the optimal ligand density for cell attachment (2.2 µg/cm$^2$) at 1 hour (left column) and 5 hours (right column) using FITC-phalloidin.

Spreading occurred earlier on 100 nm and 125 nm ANCs compared to smaller ones. Cells on larger-sized ligand-ANCs began to exhibit stress fibers, as early as 1 hr post-seeding. Cells cultured on ligand-adsorbed substrates had some filopodial projections after 1 hour in culture. Cells on smaller-sized, functionalized carriers were round and had not begun to spread. When the culture time was extended to 5 hours, cells on ligand-adsorbed substrates appeared well-spread with well defined stress fibers, whereas cells on ligand-functionalized nanocarriers appear elongated. As the size of the ANC was decreased, the presence of stress fibers decreased until they were barely visible on the smallest size carriers. On larger-sized nanocarriers, the cells appeared elongated and well attached with well-defined stress fibers. Cells cultured on unfunctionalized controls did not spread and attach, while cells seeded on whole-length fibronectin demonstrated a polarized morphology consistent with migrating cells. Spreading on the fibronectin fragment was roughly equivalent to that on the whole length molecule.

Example 10

Nanocarrier Mobility underlying Matrix Assembly

Figure 8A:
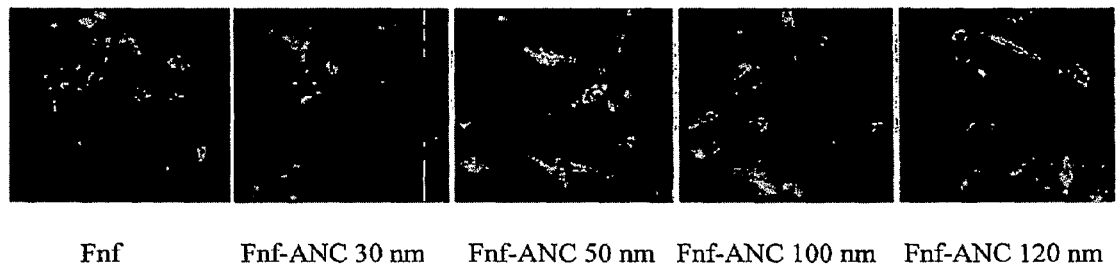

Previous studies examining epithelial cell response to ANC's demonstrated that nanocarrier mobility significantly influenced phenotypic behavior. To examine the influence of nanocarrier mobility on fibroblast behavior, substrates were plasma treated prior to ligand-ANC seeding to immobilize the nanocarriers. Minimal assembly of fibronectin was observed from cells on the immobilized carriers (FIG. 8a). F-actin labeling with rhodamine-phalloidin demonstrated no obvious differences in morphology among the conditions when carriers are immobilized. Immunolabeling of fibronectin demonstrates that mobility of the carriers is necessary for matrix assembly to occur.

Figure 8B:
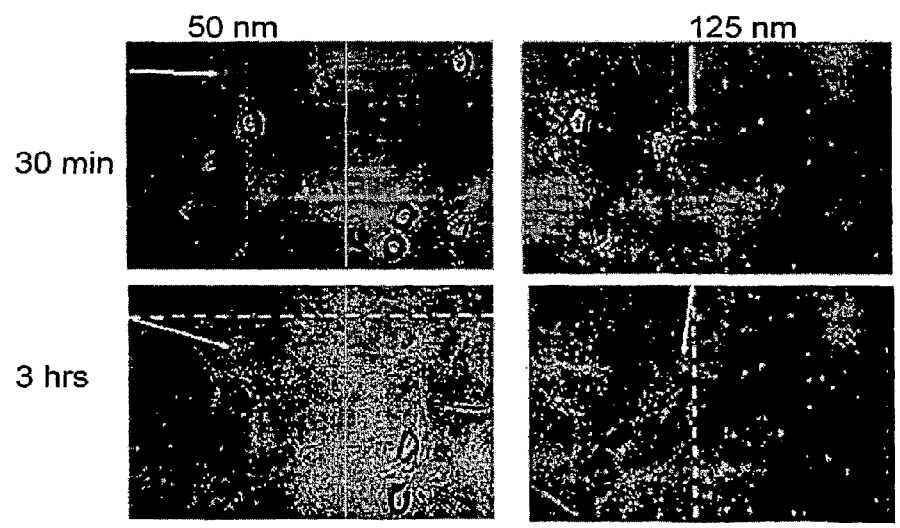

Parallel time-lapse studies of the displacement of fluorescently-labeled nanocarriers revealed that smaller-sized carriers traveled a greater distance more than larger-sized ones 6 hrs after seeding (FIG. 8b, which is a representative overlay images of fluorescent ligand-ANC (green) and fibroblasts at two time points during the time lapse tracking on fluorescently-labelled ANCs. Top row: represents 30 minutes post seeding. Bottom row represents 3 hours post seeding. Dashed lines in bottom row provide references for comparison relative to initial time point). Immobilized carriers were not displaced during this time period (FIG. 8b inset). Transmitted images taken in parallel showed that fibroblasts on smaller-sized functionalized carriers were round early in the time lapse, and began to spread and reach an elongated morphology by the end.

Cells on larger functionalized carriers were already spread at the first time point and appeared contracted and elongated by the end (FIG. 8c). Tracking and quantification of particle movements for the various conditions revealed that carrier mobility decreased with increasing carrier size.

Example 11

Atomic Force Microscopy

Figure 9:
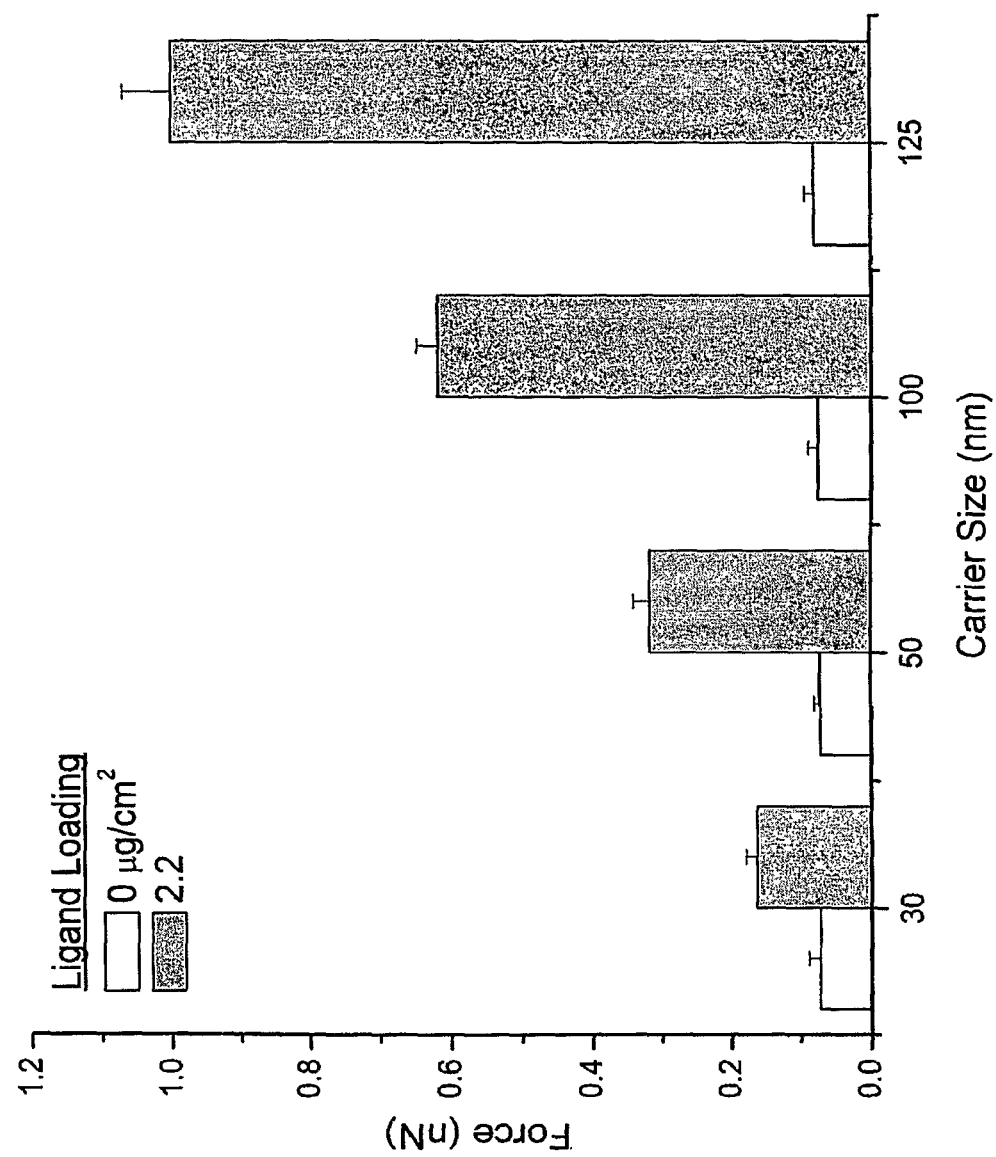
FIG. 9 is an illustration of relationship between adhesion forces and ANCs of different sizes.

To quantify the effect of carrier size on translocation of ligand-ANCs, silicon nitride cantilevers were functionalized with ligand-ANCs and brought into contact with fibroblasts that were cultured on glass slides. Force curves between various sized ligand-ANCs at the highest ligand density and fibroblasts indicate that larger forces are generated in the cantilever during detachment between single adherent fibroblasts and the tips functionalized with larger-sized ligand-ANCs compared to the forces between cells and smaller ligand-carriers (FIG. 9). Unfunctionalized carriers exhibited small forces that were distinguishable from each other. In this experimental design, various sized ligand-ANCs (30, 50, 100, and 125 nm) were functionalized to silicon nitride cantilevers by adsorbing overnight and unbound ligand-ANCs were washed off. A Digital Instruments Nanoscope IIIa was used to generate force curves between derivatized cantilevers with a spring constant of 0.38 N/m and fibroblasts in the fluid phase. Before the force curves are generated, the cells are visualized at 10× and the centered in the region of the laser path. Force curves represent an attraction between the integrin receptor on the cell and the ligand on the carrier. As the functionalized carrier size increases, the force between the cell and the cantilever also increases, indicating it is harder to break bond between the cell and the cantilever. No change in force was observed with unfunctionalized carriers.

The maximum matrix assembly occurs with the largest-sized nanocarrier and increased force between the ligand and the cell. Larger nanocarrier sized correspond to less compliant substrates and increase forces between the ligand and the cell indicate the movement of the ligand-ANC will be reduced.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

We claim:

1. A substrate comprising a substrate surface and a composition comprising a ligand of α5β1 integrin attached to a surface of a protein nanoparticle composed of a protein, with a proviso that the protein is not fibronectin, wherein the ligand comprises the sequences of SEQ ID NO: 1 and SEQ ID NO: 2, and wherein the composition is non-functionally immobilized to the substrate surface.

2. The substrate of claim 1, wherein the ligand is a fibronectin fragment comprising SEQ ID NO: 1 and SEQ ID NO: 2.

3. The substrate of claim 1, wherein the protein is albumin.

4. The substrate of claim 1, wherein the nanoparticle has a size of at least about 100 nm.

5. The substrate of claim 4, wherein the nanoparticle has a size of between about 100 nm and about 200 nm.

6. The substrate of claim 1, comprising at least about $2.5 \times 10^{-4}$ ng of the ligand per square centimeter of the surface of the nanoparticle.

7. The substrate of claim 1, which increases an assembly of fibronectin into fibronectin matrix fibrils by at least about 40%, compared to the fibronectin fragment alone.

8. The substrate of claim 7, wherein the composition is adsorbed onto a surface of the substrate.

9. The substrate of claim 1, comprising at least about 0.4 µg of the ligand per square centimeter of a surface of the substrate.

10. The substrate of claim 1, comprising at least between about 0.4 µg and about 2.2 µg of the ligand per square centimeter of a surface of the substrate.

11. The substrate of claim 1, wherein the substrate is derived from a biodegradable material.

12. The substrate of claim 1, wherein cells attached to the substrate have shape factor of at least about 6.

13. The substrate of claim 1, wherein the nanoparticle has size between about 100 nm and about 150 nm.

14. A method of promoting an assembly of a fibronectin matrix in an area of a subject comprising administering an effective amount of the substrate of claim 1 to the area.

15. The method of claim 14, wherein the composition is adsorbed onto a surface of the substrate.

* * * * *

UNITED STATES PATENT AND TRADEMARK OFFICE
CERTIFICATE OF CORRECTION

PATENT NO. : 8,715,718 B2  
APPLICATION NO. : 12/373671  
DATED : May 6, 2014  
INVENTOR(S) : Prabhas V. Moghe et al.

Page 1 of 1

It is certified that error appears in the above-identified patent and that said Letters Patent is hereby corrected as shown below:

In the Specification

Column 1 Lines 8-10 Delete the Statement of Federally Funded Research and replace with:
"This invention was made with government support under grant number DGE0333196 awarded by the National Science Foundation and grant numbers T32 HL007941, EB001046, GM059383, and CA044627 awarded by the National Institutes of Health. The government has certain rights in the invention."

Signed and Sealed this
Ninth Day of June, 2020

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 3
<212> TYPE: PRT
<213> ORGANISM: Artificial
<220> FEATURE:
<223> OTHER INFORMATION: Synthetic peptide

<400> SEQUENCE: 1

Arg Gly Asp
1

<210> SEQ ID NO 2
<211> LENGTH: 5
<212> TYPE: PRT
<213> ORGANISM: Artificial
<220> FEATURE:
<223> OTHER INFORMATION: Synthetic peptide

<400> SEQUENCE: 2

Pro His Ser Arg Asn
1               5

<210> SEQ ID NO 3
<211> LENGTH: 184
<212> TYPE: PRT
<213> ORGANISM: Artificial
<220> FEATURE:
<223> OTHER INFORMATION: Synthetic Peptide

<400> SEQUENCE: 3

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
```

|  |  |  | 20 |  |  | 25 |  |  |  | 30 |  |  |
|---|---|---|---|---|---|---|---|---|---|---|---|---|
| Arg | Ile | Arg | His | His | Pro | Glu | His | Phe | Ser | Gly | Arg | Pro | Arg | Glu | Asp |
|  |  |  | 35 |  |  |  | 40 |  |  |  |  | 45 |
| Arg | Val | Pro | His | Ser | Arg | Asn | Ser | Ile | Thr | Leu | Thr | Asn | Leu | Thr | Pro |
|  |  |  | 50 |  |  |  | 55 |  |  |  |  | 60 |
| Gly | Thr | Glu | Tyr | Val | Val | Ser | Ile | Val | Ala | Leu | Asn | Gly | Arg | Glu | Glu |
| 65 |  |  |  |  | 70 |  |  |  |  | 75 |  |  |  |  | 80 |
| Ser | Pro | Leu | Leu | Ile | Gly | Gln | Gln | Ser | Thr | Val | Ser | Asp | Val | Pro | Arg |
|  |  |  |  | 85 |  |  |  |  | 90 |  |  |  |  | 95 |
| Asp | Leu | Glu | Val | Val | Ala | Ala | Thr | Pro | Thr | Ser | Leu | Leu | Ile | Ser | Trp |
|  |  |  | 100 |  |  |  |  | 105 |  |  |  | 110 |
| Asp | Ala | Pro | Ala | Val | Thr | Val | Arg | Tyr | Tyr | Arg | Ile | Thr | Tyr | Gly | Glu |
|  |  |  | 115 |  |  |  | 120 |  |  |  | 125 |
| Thr | Gly | Gly | Asn | Ser | Pro | Val | Gln | Glu | Phe | Thr | Val | Pro | Gly | Ser | Lys |
|  |  | 130 |  |  |  |  | 135 |  |  |  |  | 140 |
| Ser | Thr | Ala | Thr | Ile | Ser | Gly | Leu | Lys | Pro | Gly | Val | Asp | Tyr | Thr | Ile |
| 145 |  |  |  |  |  | 150 |  |  |  |  | 155 |  |  |  | 160 |
| Thr | Val | Tyr | Ala | Val | Thr | Gly | Arg | Gly | Asp | Ser | Pro | Ala | Ser | Ser | Lys |
|  |  |  |  | 165 |  |  |  |  | 170 |  |  |  | 175 |
| Pro | Ile | Ser | Ile | Asn | Tyr | Arg | Thr |
|  |  |  | 180 |